US007972816B2

(12) United States Patent
Takagi et al.

(10) Patent No.: US 7,972,816 B2
(45) Date of Patent: Jul. 5, 2011

(54) EFFICIENT PROCESS FOR PRODUCING DUMBBELL DNA

(75) Inventors: Yasuomi Takagi, Chiba (JP); Kazunari Taira, Ibaraki (JP); Masumi Taki, Ibaraki (JP); Yoshio Kato, Ibaraki (JP); Makoto Miyagishi, Ibaraki (JP)

(73) Assignee: National Institute of Advanced Industrial Science and Technology, Chiba (JP)

( * ) Notice: Subject to any disclaimer, the term of this patent is extended or adjusted under 35 U.S.C. 154(b) by 847 days.

(21) Appl. No.: 10/567,168

(22) PCT Filed: Aug. 9, 2004

(86) PCT No.: PCT/JP2004/011449
§ 371 (c)(1),
(2), (4) Date: Dec. 20, 2007

(87) PCT Pub. No.: WO2005/014810
PCT Pub. Date: Feb. 17, 2005

(65) Prior Publication Data
US 2008/0153763 A1 Jun. 26, 2008

(30) Foreign Application Priority Data

Aug. 8, 2003 (JP) .................................. 2003-206905

(51) Int. Cl.
*C12P 19/34* (2006.01)
*C12Q 1/68* (2006.01)
*C07H 21/04* (2006.01)
(52) U.S. Cl. .......... 435/91.2; 435/6; 536/23.1; 536/24.5
(58) Field of Classification Search ........................ None
See application file for complete search history.

(56) References Cited

U.S. PATENT DOCUMENTS
6,451,563 B1 9/2002 Wittig

OTHER PUBLICATIONS

Scherr et al. (Cell Cycle, 2:3, 2003, pp. 251-257).*
English translation of the International Preliminary Report on Patentability for PCT/JP2004/011449 mailed May 18, 2006.
Taki M. et al., Small-interfering-RNA expression in cells from a dumbbell-shaped DNA., Angewandte Chemie, International Edition, 2004, vol. 43, No. 24, pp. 3160 to 3163.
Taki M. et al., A direct and efficient synthesis method for dumbbell-shaped linear DNA using PCR in vitro., Nucleic Acid Res. Suppl., 2003, 30th, No. 3, pp. 191 to 192.
Schakowski F. et al., A novel minimal size vector (MIDGE) improves transgene expression in colon carcinoma cells and avoids transfection of undesired DNA. Molecular Therapy, 2001, vol. 3, No. 5, pp. 793 to 800.
Simmen K.A. et al., Complex requirements for RNA polymerase III transcription of the Xenopus U6 promoter. Nucleic Acids Res. 1990, vol. 18, No. 19, pp. 5649, 5657.

* cited by examiner

*Primary Examiner* — Amy Bowman
(74) *Attorney, Agent, or Firm* — DLA Piper LLP (US)

(57) ABSTRACT

The present invention provides a simple method for producing a dumbbell-shaped DNA.
A method for producing a dumbbell-shaped DNA, wherein each of sense and antisense strands is connected at both the 5' and 3' ends of a linear-shaped double stranded DNA by a single stranded DNA of loop structure, comprising the steps of;

1) amplifying a target DNA in a template DNA by PCR using sense and antisense primers, wherein each of the sense and antisense primers contains the following sequence (a) at the 5' end and also contains the following sequences (b), (c), and (d) in order from the 5' end to the 3' end,
  (a) a part of a sense sequence of a nickase recognition sequence, comprising the sequence of a region between the site where a nick is introduced by the action of a nickase and the 3' end,
  (b) a sequence capable of forming a loop structure from a single strand,
  (c) the entire antisense sequence of the nickase recognition sequence (a),
  (d) a sequence complementary to all or part of the sequence of the target DNA;
2) treating the amplified DNA product of step 1) with a nickase of (a);
3) heating and then annealing the nickase treated amplified DNA product of step 2); and
4) treating the heated and annealed amplified DNA product of step 3) with DNA ligase, wherein the sense and antisense primers used in step 1) are phosphorylated at the 5' end, or the amplified DNA product is phosphorylated at the 5' end after step 1) but before step 4).

10 Claims, 8 Drawing Sheets

Fig. 5
A: plasmid vector targetted against EGFP
B: no vector (mock transfection)
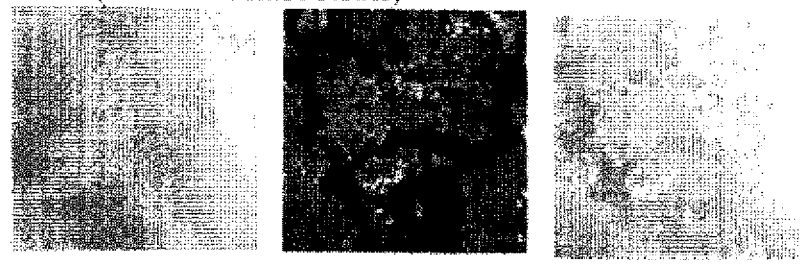
C: dumbbell vector targetted against lamin
D: dumbbell vector targetted against EGFP
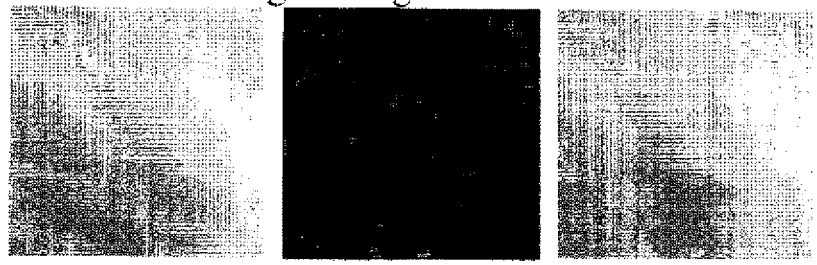
E: linear vector targetted against EGFP
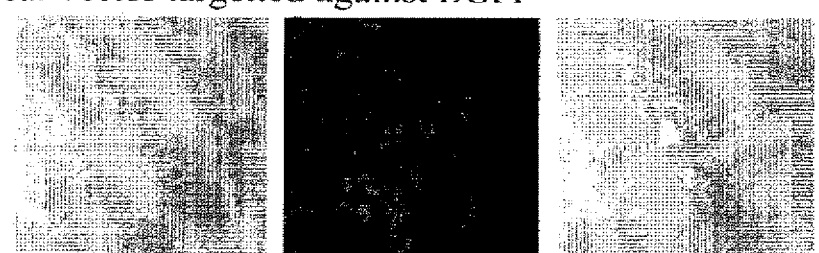
phase contrast      GFP      superposed Fig. 8
a) Tandem-type
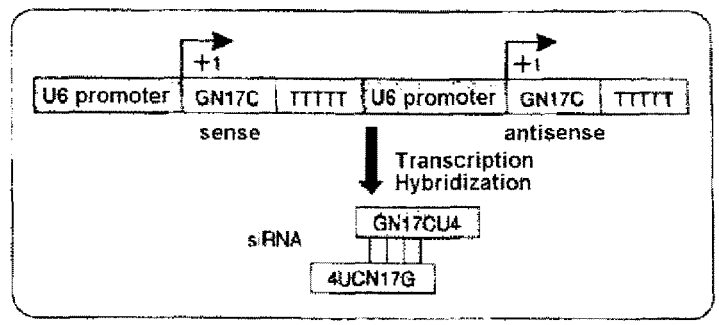
b) Stem loop-type
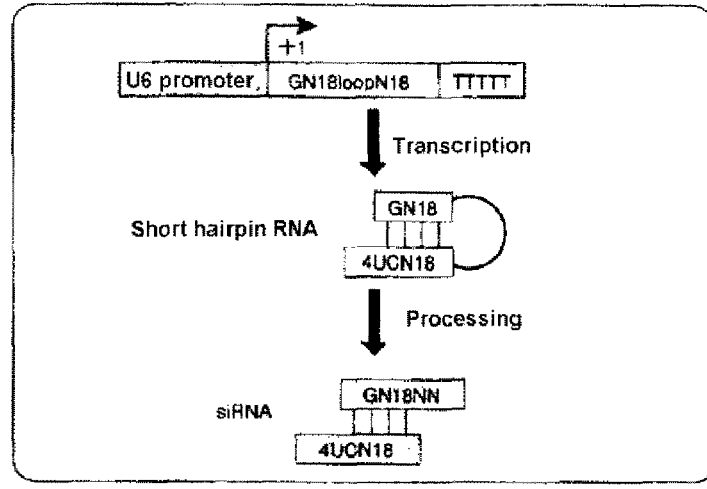

Fig. 9
(a) Efficiency of siRNA expression by a minimized promoter
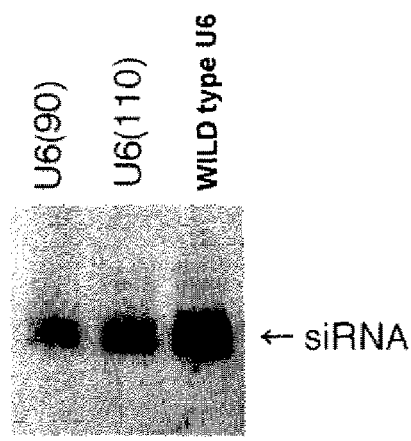
(b) Suppression of gene expression by a minimized promoter
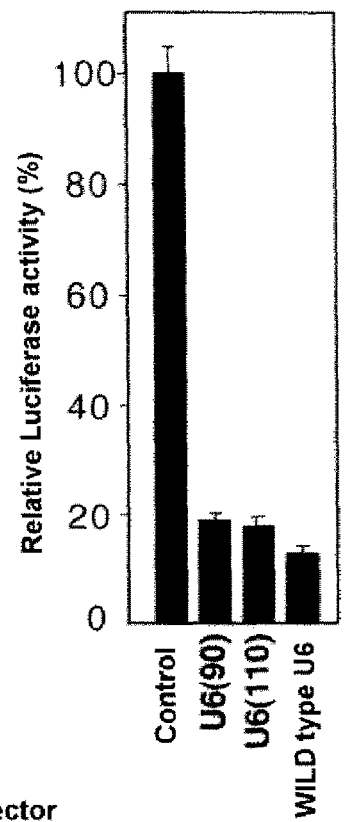
(c) Cell nucleus permeability of a minimized vector
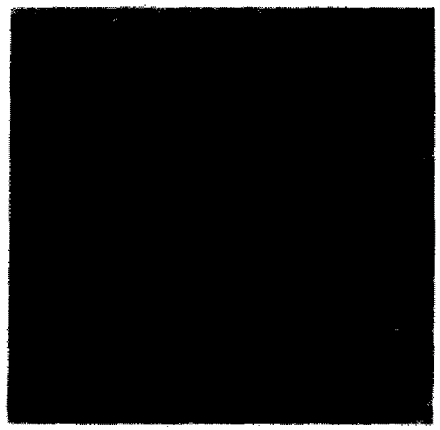
U6 (90) promoter
Wild type U6 promoter

EFFICIENT PROCESS FOR PRODUCING DUMBBELL DNA

TECHNICAL FIELD

The present invention relates to a method for producing a dumbbell-shaped DNA.

BACKGROUND ART

With the advances in the human genome project, many disease causing genes have been identified. As a result, the administration of [genes] as drugs into the human body for effective treatment, so called, [gene therapy], has become attractive (non patent reference 1). In gene therapy, the tools which introduce therapeutic genes into cells requiring treatment are called [vectors], and virus and plasmid vectors are mostly being used for real clinical studies at the present time.

Viruses deficient in pathogenicity are typically used as viral vectors. In this case, the function of the virus by which it transfers its own genes into cells by infection is utilized. Therefore, these vectors have an advantage in that they can transfer genes more efficiently into cells compared with other vectors. However, viral vectors on rare occasions can be contaminated with viruses which have escaped from pretreatment (inactivation) steps performed to remove their pathogenicity, and become pathogenic and proliferate freely as side effects. Furthermore, they have considerable problems including the occurrence of unexpected genetic recombination and the possession of immunogenicity.

Plasmid DNA (pDNA) is becoming attractive as an alternative vector in recent years, with low immunogenicity compared to viruses, and high productivity. However, recent research has revealed that if the sequence known as the CpG motif exists in the plasmid DNA, macrophage or dendritic cells can recognize the motif as a stress signal, causing induction of an immune activation reaction including the production of various inflammatory cytokines. Inflammatory cytokines lower gene expression because of their cytotoxicity; therefore, they are not suitable for gene therapy. Furthermore, plasmid DNAs usually contain antibiotic resistance genes and extra gene sequences derived from other species such as bacteria. These genes are not only undesirable for gene therapy but also have a potential to cause side effects, such as expression of undesirable proteins coded by these genes, and production of abnormal genomic DNA by incorporation of these genes into normal genomic DNA (non-patent reference 2).

Gene transfer technology (MIDGE technology) using a Minimalistic Immunogenically Defined Gene Expression (MIDGE) vector, that is, a dumbbell-shaped DNA is disclosed in the description of U.S. Pat. No. 6,451,593. This vector is the template DNA for RNA transcription, and the DNA is a circular stranded DNA which is able to form a dumbbell shape.

The circular strand of this dumbbell-shaped DNA vector comprises a first complementary sequence, a first noncomplementary sequence, a second complementary sequence, and a second noncomplementary sequence. The first and second complementary sequences pair to form a double strand. The double strand contains a promoter sequence, a coding sequence, and a polyA or a stabilizing sequence. Moreover, the first and second noncomplementary sequences form single-strand-loops. (patent reference 1).

A dumbbell-shaped DNA vector was constructed as a superior alternative vector which reduces the disadvantages and enhances the advantages of viral and plasmid vectors (non-patent reference 3). The dumbbell-shaped DNA contains only promoter and transcription sequence regions, as shown in FIG. 1. Therefore, immunogenicity can be minimized because it does not contain extra sequences. Furthermore, the closed circular DNA which is produced by creating loops at both ends of the desired gene sequence is not affected by Exonuclease (Exo-type nucleic acid digestive enzyme) activity when it is transfected into cells. Thus, it is known that the dumbbell-shaped DNA is resistant to digestion and relatively stable in serum and cells. Moreover, a method is known for producing a dumbbell-shaped DNA containing only necessary and minimal gene sequences for gene therapy by ligation of three molecules, as shown in FIG. 6 (non-patent reference 4). In the general method for producing the dumbbell-shaped DNA shown in FIG. 6, the linear-shaped target DNA fragment is amplified by PCR (step 1 (PCR) in FIG. 6) using cDNA containing a target gene sequence as a template DNA, and then both ends of the linear-shaped target DNA fragment are digested with restriction enzymes. In the general method, this fragment and two synthesized DNA fragments which contain the loop region of the dumbbell are ligated by DNA ligase to construct the dumbbell-shaped DNA.

However, a disadvantage of this production method is that the ligation reaction (step 4 in FIG. 6 (intermolecular ligation)) involves ligation of three molecules, and moreover, ligation efficiency is low because the reaction is an intermolecular ligation reaction. Furthermore, the molar concentration of each of the two synthesized DNA fragments containing the loop regions of the dumbbell needs to be in a large excess compared to the molar concentration of the linear-shaped target DNA fragment. Therefore, almost all the synthesized DNA containing the loop regions is wasted without being ligated. Moreover, this can hamper the purification process. As a result, recovery of the target dumbbell-shaped DNA becomes low.

Another method for producing the dumbbell-shaped DNA vector in vitro is as follows;

As shown in FIG. 7, two inverted N.Bpu10I nickase recognition sequences are connected at both ends of the linear-shaped target DNA fragment, using cDNA as a template. The fragment is then subcloned into a plasmid vector DNA which is amplifiable in *E. coli* and the resulting vector is then transformed into *E. coli* for large scale amplification. Then, treatment as in 6~9 in FIG. 7 is performed to construct the dumbbell-shaped DNA vector containing a target DNA, and the dumbbell-shaped DNA derived from the plasmid vector is digested and purified. However, the disadvantage of this production method is that the process is very complicated and time consuming because it requires processes such as subcloning and digestion of the plasmid vector derived dumbbell-shaped DNA.

Patent Reference 1: U.S. Pat. No. 6,451,593 Specification

Non-patent Reference 1: Verma, I. M.; Somia, N. Nature 1997, 389, 239-242.

Non-patent Reference 2: Luo, D.; Saltzman, W. M. Nat. Biotechnol. 2000, 18, 33-37. Ferber, D. Science 2001, 294, 1638-1642. Medzhitov, R. Nat. Immunol. 2001, 2, 15-16.

Non-patent Reference 3: Schakowski, F.; Gorschluter, M.; Junghans, C; Schroff, M.; Buttgereit, P; Ziske, C; Schottker, B.; Konig-Merediz, S. A; Sauerbruch, T; Wittig, B.; Schmidt-Wolf, I. G. Mol. Ther. 2001, 3, 793-800.

Non-patent Reference 4: Zanta, M. A.; Belguise-Valladier, P.; Behr, J. P. Proc. Natl. Acad. Sci. USA 1999, 96, 916.

DISCLOSURE OF THE INVENTION

Problems to be Solved by the Invention

The object of the present invention is to provide a simple method for producing a dumbbell-shaped DNA.

Means for Solving the Problems

The efficiency of producing a dumbbell-shaped DNA is significantly low by conventional methods (three-way ligation method, FIG. 6) in which ligation efficiency is approximately 40% (FIG. 3(B)). However, ligation efficiency was improved almost quantitatively (FIG. 3(A)) when a dumbbell-shaped DNA was constructed by the novel method (FIG. 1) in the present invention. As shown in FIG. 2, before the ligation reaction, compound 2c was almost completely digested by Exonuclease treatment (37° C. for 1 hour). However, after dumbbell formation, compound 4c was resistant to Exonuclease treatment (increase in stability).

PCR was performed using 2 PCR primers, one of which contained a fluorescein-label at a single site of the loop region by chemical modification. The linear-shaped DNA obtained by PCR was subjected to dumbbell modification by the method of the present invention followed by polyacrylamide gel electrophoresis for analysis. The modified dumbbell-shaped DNA, which contained a fluorescein-label at a single site in the loop region, showed resistance to exonuclease and its stability was increased, as shown in FIG. 2.

PCR was performed using 2 PCR primers, one of which contained an amino group at a single site in the loop region as shown in FIG. 4. The linear-shaped DNA obtained by PCR was subjected to dumbbell modification by the method of the present invention and, thus, the dumbbell-shaped DNA which contained a primary amino group at a single site in the loop region was constructed. Fluorescein-OSu was reacted with the above described dumbbell-shaped DNA and polyacrylamide gel electrophoresis was conducted for analysis. The results showed that only the primary amino group at a single site in the approximately 500 bp dumbbell-shaped DNA was site specifically modified by fluorescein. No fluorescein modification was detected in a negative control experiment using a dumbbell-shaped DNA which had the same nucleotide sequence as used in the above experiment, except that it contained no primary amino group in the loop region.

Thus, specific chemical modification of the loop region was now possible after dumbbell-modification. Moreover, this site specific modification was possible even before nickase treatment (data not shown).

Specifically, the sequence of the wild type U6 promoter, used as a promoter to express siRNA, is approximately between 240 and 400 base pairs and the sequence of wild type tRNA promoter is approximately between 100 and 150 base pairs. However, it is better for DNA used for gene transfer to be as short as possible when considering cell permeability. Therefore, cell permeability was actually examined using a U6 promoter less than 150 base pairs long. The result showed that cell permeability was indeed increased by DNA with shorter sequence (FIG. 9(c)). Thus, promoters with minimized sequences are expected to increase expression level in cells. Moreover, DNAs to be transferred can be chemically synthesized in cases where they are less than 150 base pairs.

In a method of performing transfection without using transfection agents, a loop structure of the dumbbell-shaped DNA was modified in a site-specifically manner with peptides to deliver the dumbbell-shaped DNA vector into mammalian cells. The dumbbell-shaped DNA-peptide complex in which peptide was attached by covalent bond was digested with restriction enzyme (EcoRI) followed by polyacrylamide gel electrophoresis for analysis. The formation of dumbbell-shaped DNA-peptide complex was confirmed by detecting digested fragments at various positions depending on the molecular weight of each peptide.

The present invention was accomplished based on the observations described above.

The summary of the present invention is as follows;

[1] A method for producing a dumbbell-shaped DNA, wherein each of sense and antisense strands is connected at both of the 5' and the 3' ends of a linear-shaped double stranded DNA by a single stranded DNA of loop structure, comprising the steps of:

1) amplifying a target DNA sequence within a template DNA by nucleic acid amplification using sense and antisense primers, wherein each of the sense and antisense primers contains the following sequence (a) at the 5' end and also contains the following sequences (b), (c), and (d), in order from the 5' end to the 3' end, (a) a part of a sense sequence of a nickase recognition sequence, comprising the sequence of a region between the site where a nick is introduced by the action of a nickase and the 3' end, (b) a sequence capable of forming a loop structure from a single strand, (c) the entire antisense sequence of the nickase recognition sequence (a), (d) a sequence complementary to all or part of the sequence of the target DNA;

2) treating the amplified DNA product of step 1) with a nickase of (a);

3) heating and then annealing the nickase treated amplified DNA product of step 2); and 4) treating the heated and an annealed amplified DNA product of step 3) with DNA ligase, wherein, the sense and antisense primers used in step 1) are phosphorylated at the 5' end or the amplified DNA product is phosphorylated at the 5' end after 1) but before 4).

[2] A method of [1], wherein the dumbbell-shaped DNA is used as a vector for RNA transcription.

[3] A method of [1] or [2], wherein the target DNA sequence contains at least one promoter sequence and an siRNA transcription sequence.

[4] A method of [3], wherein the dumbbell-shaped DNA is a tandem-shaped siRNA expression vector or a stem loop-type siRNA expression vector.

[5] A method of any one of [1]~[4], wherein the sense primer and/or the antisense primer contains a first spacer sequence and a second spacer sequence, the first spacer and second spacer sequences being complementary to each other, and the first and second spacer sequences being connected so that they are in opposite directions to each other with the sequence (b) interposed.

[6] A method of any one of [1]~[5], wherein for the sense and antisense primers, the sequence (a) is $TN^1AGG$ (wherein T, A, and G represent thymine, adenine, and guanine, respectively, and $N^1$ represents any one of adenine, cytosine, guanine, or thymine), the sequence (b) is $(T)_n$ (wherein T represents thymine and n is an integer of at least one), and the sequence (c) is $CCTN^{11}AGC$ (wherein C, T, A, and G represent cytosine, thymine, adenine, and guanine, respectively, and $N^{11}$ represents any one of adenine, cytosine, guanine, or thymine).

[7] A method of [6], wherein the sense and antisense primers further contain a first and a second spacer sequence, the first and second spacer sequences in the sense primer being represented by AG and TC, respectively, and the first spacer and second spacer sequences in the antisense primer being represented by TC and AG, respectively, and in the sense and antisense primers, the first and second spacer sequences being connected so that they are in opposite directions to each other with sequence (b) interposed.

[8] A method of [7], wherein the sequence (b) is represented by TTTT in the sequences of the sense and antisense primers.

[9] A method of any one of [1]~[8], wherein the sense primer and/or the antisense primer is modified by a functional group in at least one position of the nucleic acid backbone or bases of sequence (b) and/or the spacer sequence.

[10] A method of [9], further comprising a step of substituting a functional group after step 1).

[11] A composition containing at least one pair of primers consisting of sense and antisense primers, wherein each of the sense and antisense primers contains the following sequence (a) at the 5' end and also contains the following sequences (b), (c), and (d) in order from the 5' end to the 3' end;
(a) a part of a sense sequence of a nickase recognition sequence, comprising the sequence of a region between the site where a nick is introduced by the action of a nickase and the 3' end;
(b) a sequence capable of forming a loop structure from a single strand;
(c) the entire antisense sequence of the nickase recognition sequence (a);
(d) a sequence complementary to all or part of the sequence of a target DNA.

[12] A composition [11] for producing a dumbbell-shaped DNA, wherein each of the sense and antisense strands is connected at both the 5' and 3' ends of a linear-shaped double stranded DNA by a single stranded DNA of loop structure.

[13] A kit for producing a dumbbell-shaped DNA, wherein each of the sense and antisense strands is connected at both the 5' and 3' ends of a linear-shaped double stranded DNA by a single stranded DNA of loop structure, the kit containing at least one pair of primers consisting of sense and antisense primers, wherein each of the sense and antisense primers contains the following sequence (a) at the 5' end and also contains the following sequences (b), (c), and (d) in order from the 5' end to the 3' end;
(a) a part of a sense sequence of a nickase recognition sequence, comprising the sequence of a region between the site where a nick is introduced by the action of a nickase and the 3' end;
(b) a sequence capable of forming a loop structure from a single strand;
(c) the entire antisense sequence of the nickase recognition sequence (a);
(d) a sequence complementary to all or part of the sequence of a target DNA.

[14] A method for producing a nucleic acid vector, comprising a delivery agent attached to a dumbbell-shaped DNA, wherein each of the sense and antisense strands is connected at both the 5' and the 3' ends of a linear-shaped double stranded DNA by a single stranded DNA of loop structure, comprising the steps of:
1) amplifying a target DNA sequence in a template DNA by PCR using a sense and an antisense primer, wherein each of the sense and antisense primers contains the following sequence (a) at the 5' end, and also contains the following sequences (b), (c), and (d) in order from the 5' end to the 3' end;
(a) a part of a sense sequence of a nickase recognition sequence, comprising the sequence of a region between the site where a nick is introduced by the action of a nickase and the 3' end,
(b) a sequence capable of forming a loop structure from a single strand;
(c) the entire antisense sequence of the nickase recognition sequence (a);
(d) a sequence complementary to all or part of the sequence of the target DNA;
2) treating the amplified DNA product of step 1) with a nickase of (a);
3) heating and then annealing the nickase treated amplified DNA product of step 2);
4) treating the heated and annealed amplified DNA product of step 3) with DNA ligase; and
5) attaching a delivery agent to a sequence other than the sequence of the target DNA in the DNA ligase treated amplified DNA product of step 4),
wherein, the sense and antisense primers used in step 1) are phosphorylated at the 5' end or the amplified DNA product is phosphorylated at the 5' end after step 1) but before step 4).

[15] A dumbbell-shaped DNA produced by a method of any one of [1]~[10].

[16] A dumbbell-shaped DNA, wherein each of sense and antisense strands is connected at both the 5' and 3' ends of a linear-shaped double stranded DNA by a single stranded DNA of loop structure, containing the following sequences (a')~(d'),
(a') a part of a sense sequence of a nickase recognition sequence, comprising the sequence of a region between the site where a nick is introduced by the action of a nickase and the 3' end,
(b') a sequence capable of forming a loop structure from a single strand,
(c') the entire antisense sequence of the nickase recognition sequence (a'),
(d') a target DNA sequence.

[17] A dumbbell-shaped DNA of [15] or [16] which can be transfected into cells or tissues so as to express a functional nucleic acid in the cells or tissues.

[18] A dumbbell-shaped DNA of [17], wherein the functional nucleic acid to be expressed is a double stranded RNA containing siRNA or a hairpin RNA.

[19] A dumbbell-shaped DNA of [17], wherein the functional nucleic acid to be expressed is a ribozyme.

[20] A dumbbell-shaped DNA of [17], wherein the functional nucleic acid to be expressed is an antisense RNA.

[21] A dumbbell-shaped DNA of any one of [17] to [22], which contains all or pan of a promoter region transcribed from RNA polymerase III.

[22] A dumbbell-shaped DNA of [21], wherein all or part of a promoter region transcribed from RNA polymerase III contains a sequence of 250 bases or less comprising at least one of the following sequences (i)~(iv):
(i) TATA (SEQ ID NO: 26)
(ii) CTTACCGTAACTTGAAAGT (SEQ ID NO: 27)
(iii) YYTCCCANNRTNCNNYGCRR (SEQ ID NO: 28)
(iv) ATGCAAAT (SEQ ID NO: 29) or the sequence complementary to the sequence.
(wherein R is either guanine or adenine, Y is either cytosine or thymine, and N is any one of guanine, adenine, cytosine, or thymine.)

[23] A dumbbell-shaped DNA of [21], wherein all or part of a promoter region transcribed from RNA polymerase III contains a sequence of 150 bases or less comprising at least one of the following sequences (i') to (ii'):

(i')                      RRYNNARYGG (ii')                    GGTTCGANTCC (wherein R is either guanine or adenine, Y is either cytosine or thymine, and N is any one of guanine, adenine, cytosine, or thymine).

[24] A dumbbell-shaped DNA of any one of [21]~[23] which contains any one of the sequences of SEQ ID NOS: 1, 22, 23 and 25.

[25] A dumbbell-shaped DNA of any one of [17]~[24], wherein the functional nucleic acid to be expressed is targeted against a gene related to a virus or cancer.

[26] A dumbbell-shaped DNA of [25], wherein the virus is selected from the group consisting of HIV, HCV, and HBV.

[27] A dumbbell-shaped DNA of [15] or [16] which can be transfected into cells or tissues so as to suppress the expression of genes.

[28] A dumbbell-shaped DNA of [27] which is a DNAzyme.

[29] A dumbbell-shaped DNA of [27] which functions as a decoy.

[30] A dumbbell-shaped DNA of any one of [15]~[29], which is a modified DNA constructed from optically active boranophosphate.

[31] A composition containing a dumbbell-shaped DNA of any one of [15]~[30]

[32] A pharmaceutical composition containing a dumbbell-shaped DNA of any one of [15]~[30]

A method of producing a dumbbell-shaped DNA according to the present invention possesses the following advantages;

1) construction of a plasmid vector DNA containing four N.Bpu101 sites, which is required for the conventional method in FIG. 7, is not necessary.

2) an undesired dumbbell-shaped DNA derived from the vector DNA which is produced in the conventional method in FIG. 7 is not constructed.

3) the method of the present invention in FIG. 1 requires only two synthetic oligomers, while the conventional method in FIG. 6 requires four PCR primers (synthetic oligo DNA), therefore, the present invention is economical.

4) the ligation reaction for performing circularization to create a dumbbell-shaped DNA according to the present invention in FIG. 1 is an intramolecular reaction, therefore, the efficiency is very high, resulting in an increased amount of recovery compared with the conventional method.

The recovery rate of circularized DNA is approximately 40% in the conventional method (based on double stranded DNA) while it is approximately 80% in the present invention. That is, in step 4 of FIG. 6, only approximately 4% of the synthetic oligo DNA containing a functional group or an active site in the loop region becomes a dumbbell-shaped DNA, and the remaining 96% is wasted.

However, a vast majority of the PCR primers is theoretically incorporated by the reaction and are not wasted by introducing a functional group or an active site into the PCR primers. Moreover, the ligation reaction is an intramolecular reaction, therefore, a majority (approximately 80~95%) of the synthetic oligo DNAs containing a functional group or active site forms a dumbbell-shaped DNA. Thus, it is beneficial to introduce a functional group or an active site in the single stranded loop-region (somewhere in TTTT in the case of FIG. 1), of either upstream or downstream PCR primers, or both.

5) the procedure is extremely simple due to being a one-pot reaction, wherein procedures 2 to 5 in FIG. 1 can be performed entirely in one tube.

6) the conventional method involving PCR reaction as shown in FIG. 6 requires two purification steps, while the method of the present invention shown in FIG. 1 requires only the last purification (step 6). The elimination of one purification step prevents an overall low recovery of dumbbell-shaped DNA.

[A dumbbell-shaped DNA] as used herein means DNA, wherein the sense and antisense strands are connected by a loop-structured single stranded DNA at both the 5' and 3' ends of the linear-shaped double stranded DNA. The DNA comprising a dumbbell-shaped DNA can either be modified (modified DNA) or unmodified (wild type DNA) at bases, phosphate groups, or sugar moieties, at the 5' end and/or the 3' end.

The types of modified DNAs and methods of making them are listed in the literature. Specifically, modified DNAs in which a hydroxyl group (—OH) attached to the phosphorus in the phosphate group is substituted with a group selected from the group consisting of a borano group (—$BH_3$), thiol group (—$S^-$), amino group (—$NH_2$), lower alkyl group (—R) (R includes, for example, methyl group, ethyl group) and alkoxyl group (—OR) (R includes, for example, methyl group, ethyl group) are described in Biochemistry (1979) 18, 5134.; Tetrahedron Lett. (1982) 23, 4289. Modified DNAs in which an oxo group (═O) attached to the phosphorus in the phosphate group is substituted with a thioxo group (═S) are described in Tetrahedron Lett. (1980) 21, 1121; Biochemistry (1987) 26, 8237. Modified DNAs in which the oxy group (—O—) attached to the phosphorus in the phosphate group and the carbon at the 5' position of a sugar moiety is substituted with a group selected from the group consisting of a methylene group (—$CH_2$—), thioxy group (—S—), and amino group (—NH—), are described in Nucleic Acids Res. (1997) 25, 830. Modified DNAs in which the oxy group (—O—) attached to the phosphorus in the phosphate group and the carbon at the 3' position of a sugar moiety is substituted with a group selected from the group consisting of a methylene group (—$CH_2$—), thioxy group (—S—), and amino group (—NH—), are described in Proc. Natl. Acad. Sci. USA (1995) 92, 5798. Modified DNAs in which the phosphate group is substituted with phosphorodithioate is described in Tetrahedron Lett. (1988) 29, 2911; JACS (1989) 111, 2321.

Examples of modified bases include, but are not limited to, 2-aminopurine, 2'-amino-butyryl pyrene-uridine, 2'-aminouridine, 2'-deoxyuridine, 2'-fluoro-cytidine, 2'-fluoro-uridine, 2,6-diaminopurine, 4-thio-uridine, 5-bromo-uridine, 5-fluoro-cytidine, 5-fluorouridine, 5-indo-uridine, 5-methyl-cytidine, inosine, N3-methyl-uridine, 7-deaza-guanine, 8-aminohexyl-amino-adenine, 6-thio-guanine, 4-thio-thymine, 2-thio-thymine, 5-iodo-uridine, 5-iodo-cytidine, 8-bromo-guanine, 8-bromo-adenine, 7-deaza-adenine, 7-diaza-guanine, 8-oxo-guanine, 5,6-dihydro-uridine, and 5-hydroxymethyl-uridine. These synthetic units are commercially available; (for example, purchased from Glen Research Company) and can be incorporated into DNA by chemical synthesis.

Examples of modification of the sugar moiety are 3'-deoxylation, 2'-fluorination, and arabanosidation, however, it is not to be construed as being limited thereto. Incorporation of these into DNA is also possible by chemical synthesis.

Examples of the 5' end modification are 5'-amination, 5'-biotinylation, 5'-fluoresceinylation, 5'-tetrafluoro-fluoreceinylation, 5'-thionation, and 5'-dabsylation, however it is not to be construed as being limited thereto.

Examples of the 3' end modification are 3'-amination, 3'-biotinylation, 2,3-dideoxidation, 3'-thionation, 3'-dabsylation, 3'-carboxylation, and 3'-cholesterylation, however, it is not to be construed as being limited thereto.

Existing DNA is called [template DNA] in cases where the primary structure of the existing DNA determines the primary structure of the synthesized DNA in a DNA synthetic reaction.

Nickase is a site or strand specific endonuclease artificially synthesized by engineering methods.

[A nick] is DNA damage caused by endonuclease activity in which a phosphodiester bond in one strand of a double stranded DNA is broken, forming a phosphate group at the 5' end and a hydroxyl group at the 3' end. The break can be repaired by DNA ligase.

[A nickase recognition sequence] is a DNA sequence which is recognized by nickase to have a nick created at a specific site in the sequence.

[Annealing] is the reforming of a double stranded DNA from single stranded DNAs created by denaturation of the double stranded DNA. A double stranded DNA may be formed either between two molecules (that is, between two DNA strands) or intramolecularly (that is, within a single DNA strand). In the method of constructing a dumbbell-shaped DNA in the present invention, annealing occurs by an intramolecular reaction and a double stranded DNA and loop regions are newly formed.

[A promoter] is a type of regulatory gene which contains a region where RNA polymerase binds and transcription of an operon starts.

[siRNA] is a short double stranded oligonucleotide possessing RNA interfering ability (that is, the ability to disrupt a target mRNA). The RNA strand which recognizes the target mRNA is an antisense strand and the other RNA is a sense strand. Generally, the [antisense strand] is a RNA strand which recognizes mRNA. The number of bases of siRNA is generally 50 or less, preferably, between 10 and 40, more preferably, between 10 and 30. Moreover, siRNA is not limited to RNA molecules and it may be a chimera molecule consisting of a RNA molecule and another nucleotide (for example, DNA). It may be a substituted or modified form of these molecules. Examples of substituted or modified forms of RNA and DNA molecules are molecules in which the 5' end is 5' monophosphorylated and 2' hydroxyl group at the 3' end is substituted with 2'-deoxy, 2'-O-methyl, biotin, 2',3'-dideoxcytosine, and aminopropylphosphoester.

[siRNA transcription sequence] means the DNA sequence which codes for siRNA. The siRNA transcription sequence contains both the DNA sequence which codes for a sense strand of siRNA and the DNA sequence which codes for an antisense strand of siRNA. In a siRNA expression vector carrying a siRNA transcription sequence, a vector which contains 2 promoters, wherein one promoter is functionally connected to the DNA sequence encoding a sense strand of siRNA and the other promoter is functionally connected to the DNA sequence encoding an antisense strand of siRNA, the two DNA sequences coupled in tandem, is called [a tandem-type siRNA expression vector] (FIG. 8 (a)). Moreover, a vector, wherein a promoter sequence is functionally connected to a DNA sequence encoding a sense strand of siRNA and a DNA sequence encoding an antisense strand of siRNA, the two DNA sequences being positioned so that they are in opposite directions to each other, and with an optional sequence interposed (for example, sequences which can form a loop structure by a single strand) (FIG. 8 (a)), is called [a stem-loop shaped siRNA expression vector].

[Functionally connected] means that the promoter is connected to a DNA sequence encoding a sense strand of siRNA and/or a DNA sequence encoding an antisense strand so that their transcriptional products are formed in response to transcription from the promoter. Therefore, the location of the promoter with respect to the DNA sequences can be either upstream or downstream; however, it is usually located upstream. Moreover, an optional DNA sequence can be inserted between the DNA sequence and the promoter sequence as long as transcription of the DNA sequence can occur.

[A spacer sequence] is an oligonucleotide sequence which does not have a biochemical function and which exists between a single strand nucleotide sequence of a loop structure and a target DNA sequence (promoter, transcription, termination nucleotide sequences).

[Opposite directions] means positioning two sequences complementary to each other such that they are in opposite directions. For example, in the sequence AGTTTTCT, the first and second spacer sequences are positioned in opposite directions to each other with the sequence (b) placed between them, where the first spacer sequence is AG, the second spacer sequence is TC, and the sequence (b) is TTTT.

[A nucleic acid backbone] is a fundamental structure consisting of a '- - - sugar-phosphate-sugar-phosphate - - - '. A nucleic acid backbone can be either modified or unmodified.

[A base] means a purine or a pyrimidine base which composes a nucleic acid. Purine or pyrimidine bases can either be modified or unmodified.

[A delivery agent] is one of a variety of molecules which have the ability to accurately deliver a necessary amount of drug to a required place in the body, or at the right time, or both.

[A functional nucleic acid] is a nucleic acid which has a specific function in cells, tissues, and organs. Examples include nucleic acids which have physiologically active functions such as suppression of gene expression, enzymatic activities such as RNA digestion, ability to bind to proteins or RNAs, low molecular weight compounds.

[A hairpin RNA] is a RNA in which both the 5' and 3' ends of a linear-shaped double stranded RNA are connected by a single stranded RNA loop structure. A stem-loop RNA, having the stem structure and the loop structure which connects the stem structure is included. The stem structure does not have to be an exact match.

[Ribozyme] is a general term for biological catalysts in which RNA is the chemical entity.

[An antisense RNA] is an RNA molecule which contains a sequence complementary to a specific RNA. It binds complementarily to a specific target RNA and suppresses the expression of the target RNA.

[DNAzyme] is a general stem for biological catalysts in which DNA is the chemical entity.

[An optically active boranophosphate] is a boranophosphate which possesses an asymmetrical center caused by the covalent bonding of a borano group with an α-phosphorus atom at the 5' end.

It should be noted that [~] as used herein indicates a range including the numerals before and after that symbol a minimum and a maximum, respectively.

In the designations of base sequences, A, C, G, T, and U indicate adenine, cytosine, guanine, thymine and uracil, respectively and N means any one of adenine, cytosine, guanine, thymine or uracil. Base sequences shall be described in the direction from the 5' to 3', unless otherwise specified.

Effects of the Invention

The present invention simplifies the method of producing a dumbbell-shaped DNA.

The present invention covers the contents explained in the Description and/or Drawings in Japanese Patent Application No. 2003-206905, from which it claims the priority.

1) a target nucleotide sequence (a promoter and target transcription region; for example, a siRNA coding region) in a cDNA was amplified by PCR using two separate primers and purified. Each of these primers contains TNAGG, part of the Bpu101 restriction enzyme site which is phosphorylated at the 5' end, the sequence (NNTTTTNN; in this Figure AGTTTTCTT and TCTTTTGA) in which the first and second spacer sequences are connected so that they are in opposite directions to each other with a single strand loop region interposed, and CCTNAGC which is an antisense sequence of the Bpu101 restriction enzyme site.

2) a nick (cut) was created at a specific site in the nucleotide sequence by N.Bpu101 enzyme and the reaction mixture was heated and gradually cooled to room temperature to form a loop structure.

3) an intramolecular ligation reaction was performed using DNA ligase and only one type of a target dumbbell-shape DNA was synthesized. The recovery rate was significantly high due to the intramolecular reaction. (FIG. 3(A)) A single target DNA fragment was purified by DEAE ion exchange column, polyacrylamide gel electrophoresis, agarose electrophoresis, and so forth.

Figure 1:
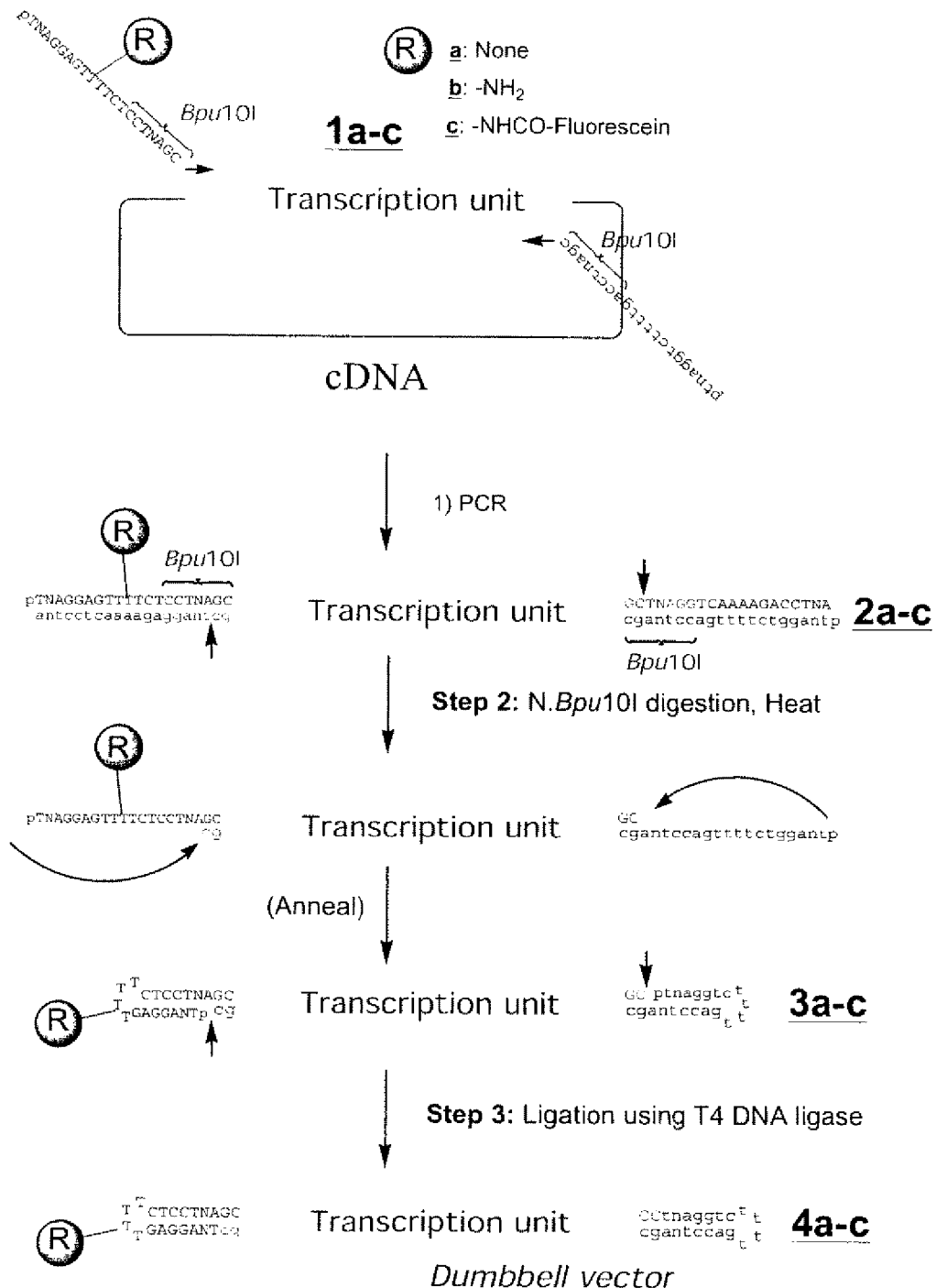
FIG. 1 shows an example of the method for producing a dumbbell-shaped DNA in the present invention. The method is especially advantageous when a functional group is attached to either one or both loop regions (in the case, the TTTT sequence region) of the upstream or downstream PCR primers. Theoretically, a PCR reaction continues until all of the PCR primers (materials) are consumed, therefore, materials are almost never wasted. All steps up to 2)-3) are one-pot reactions (reactions in which reagents are added into a test tube one after another), therefore, it is easy and simple.
Figure 2:
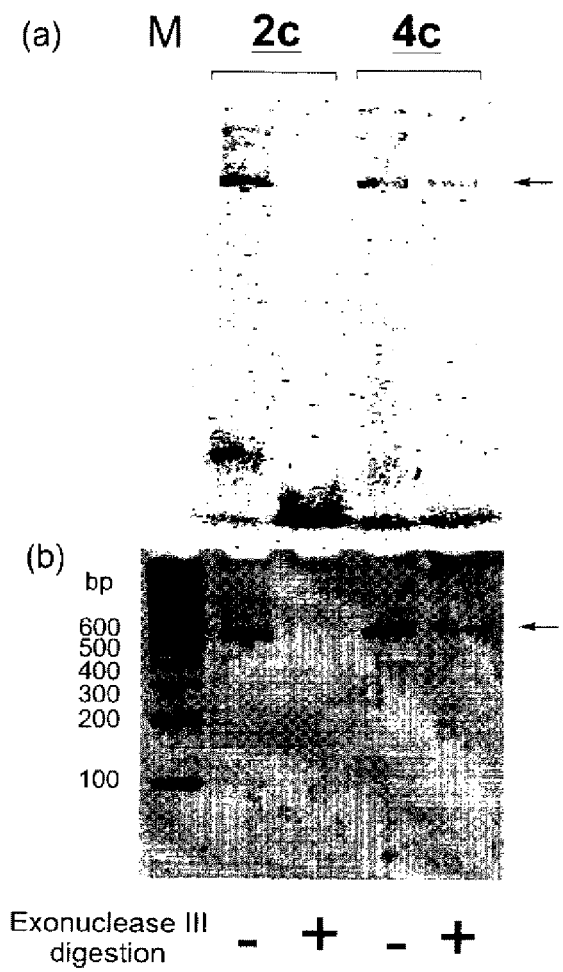

FIG. 2 shows the stability of DNA against exonuclease digestion. Bands were first visualized by (a) fluoroimager 595. Compound numbers including 2c and 4c in FIG. 1 are also applicable to this figure. The band with a size of approximately 600 bp was the DNA labeled with fluorescein. The gel was then stained with ethidium bromide and bands were visualized with a Transilluminator.

Figure 3:
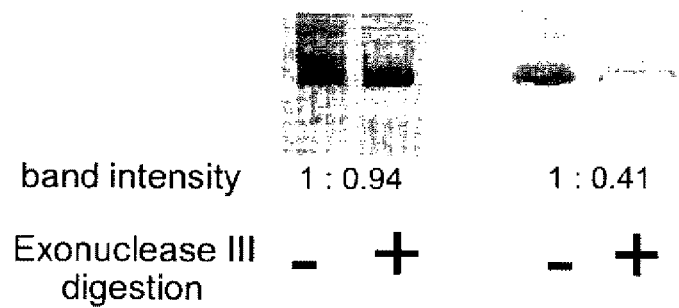

FIG. 3 shows the efficiency of transformation from a linear-stranded vector to a dumbbell-shaped vector. The gel was stained with ethidium bromide and the bands were visualized with a Transilluminator.

Figure 4:
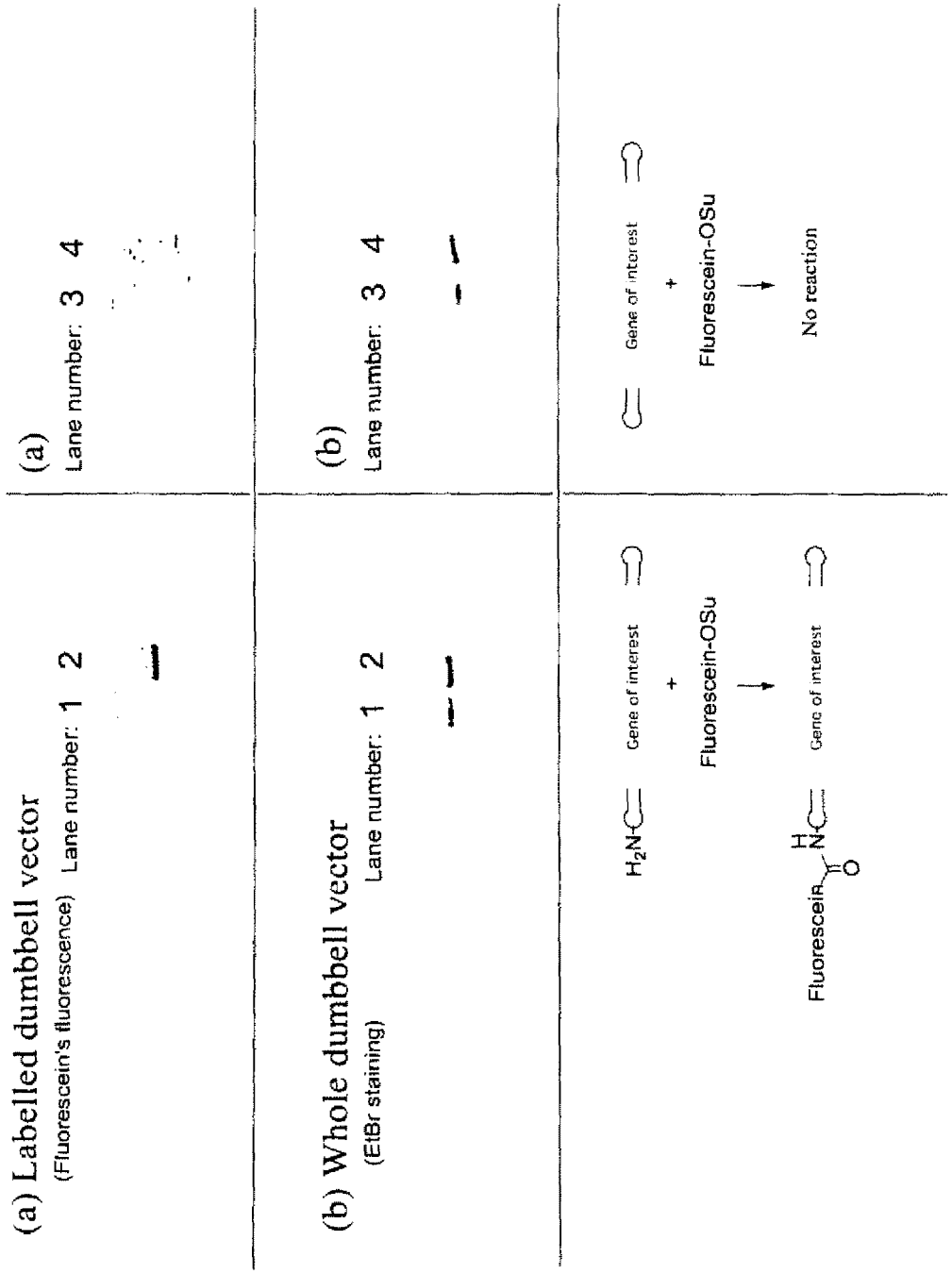

FIG. 4 shows a loop specific modification of a dumbbell-shaped DNA using a succinimide ester of fluorescein. Bands were first visualized by (a) fluoroimager 595. Then, the gel was stained with ethidium bromide and the bands were visualized with a Transilluminator. Lanes 1 and 2 contained dumbbell-shaped DNA which had a primary amino group in the hairpin loop region. Lanes 3 and 4 contained dumbbell-shaped DNA which did not have a primary amino group in the hairpin loop region. Lanes 2 and 4 contained the reaction mixture samples which were reacted with the fluorescein succinimide ester. Lanes 1 and 3 contained samples before the reaction.

FIG. 5 shows the suppression of EGFP expression by various vectors which were transfected into HeLaS3/EGFP cells.

Figure 6:
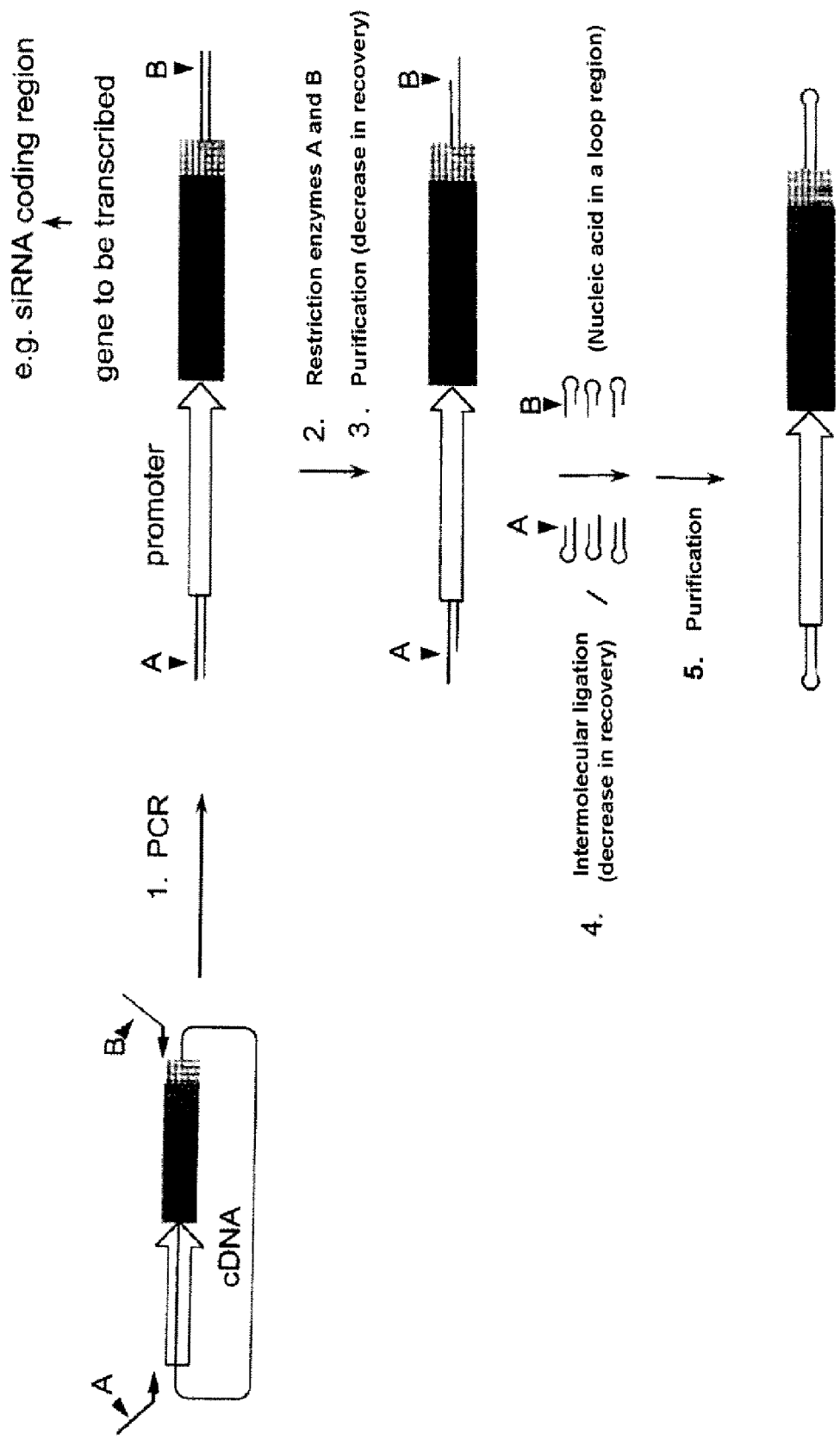

FIG. 6 shows one of the conventional methods for producing a dumbbell-shaped DNA.

1. The target nucleotide sequence (a promoter and a target transcription region; for example, a siRNA coding region) in cDNA was amplified by PCR using primers A and B. Each primer had a different restriction enzyme digestion site. The amplified nucleotide sequence was then purified.

2. The purified nucleotide sequence was treated with different restriction enzymes A and B.

3. The only specific target DNA fragment was purified by DEAE ion exchange column, polyacrylamide gel electrophoresis, agarose electrophoresis, and so forth.

4. Ligation using DNA ligase was performed between three molecules by mixing the target DNA fragment with 2 types of synthetic oligo DNAs (a loop region) at 10 fold higher amounts than the target DNA fragment to construct a dumbbell-shaped DNA. The recovery rate was low due to the intermolecular ligation (FIG. 3(B)).

5. The specific target DNA fragment was purified by DEAE ion exchange columns polyacrylamide gel electrophoresis, agarose electrophoresis, and so forth.

Figure 7:
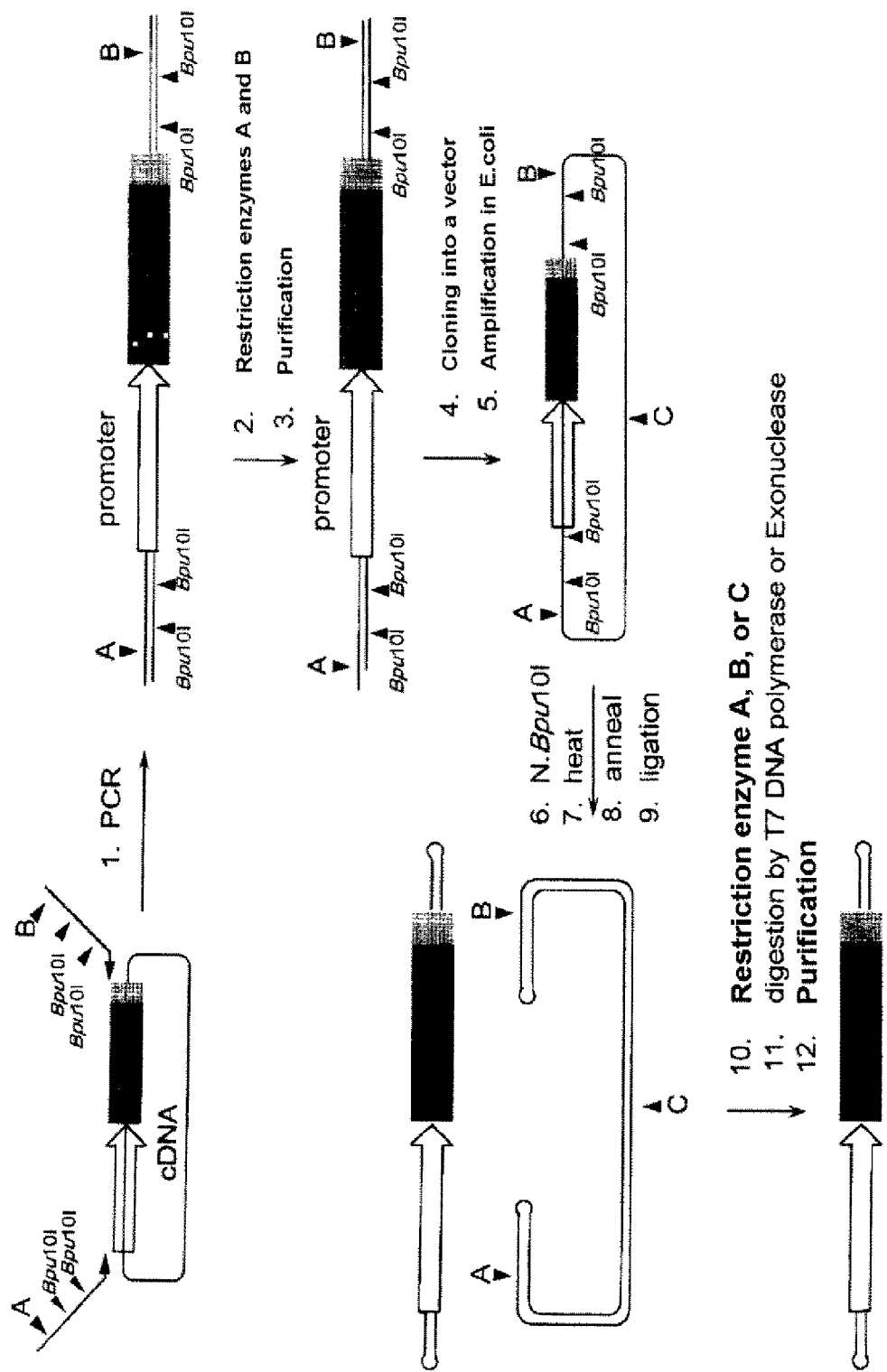

FIG. 7 shows another conventional method of producing a dumbbell-shaped DNA.

1. A target nucleotide sequence (a promoter and a target transcription region; for example, a siRNA coding region) in cDNA was amplified by PCR using primers A and B. Each primer had a different restriction enzyme digestion site and also had two Bpu101 restriction enzyme sites. The amplified nucleotide sequence was then purified.

2. The purified nucleotide sequence was treated with different restriction enzymes A and B.

3. The specific target DNA fragment was purified by DEAE ion exchange column, polyacrylamide gel electrophoresis, agarose electrophoresis, and so forth.

4. The purified target DNA fragment was cloned into an *E. coli* amplifiable vector DNA (MIDGE vector or the like), using DNA ligase.

5. *E. coli* was transformed with the plasmid DNA of 4 and the plasmid DNA carrying the target DNA fragment was amplified.

6. A nick (cut) was created specifically at a targeted nucleotide sequence using N.Bpu101.

7. The DNA of 6 was heated.

8. The reaction mixture was then gradually cooled to room temperature to form a loop.

9. Two types of a dumbbell-shaped DNA were synthesized by intramolecular ligation reaction using DNA ligase.

10. The dumbbell-shaped DNA derived from the *E. coli* amplifiable vector DNA (MIDGE vector or the like) was digested with restriction enzymes. The restriction enzyme sequence should not occur in the target DNA fragment at that time.

11. The dumbbell-shaped DNA derived from the vector DNA (MIDGE vector and such) which was partially digested with restriction enzymes was completely digested.

12. The specific target DNA fragment was purified by DEAE ion exchange column, polyacrylamide gel electrophoresis, agarose electrophoresis, and so forth.

FIG. 8 shows a schematic diagram of an example of a tandem-type siRNA expression vector (a)) and a stem loop-type siRNA expression vector (b)). A sense RNA and an antisense RNA are transcribed from two U6 promoters in a) tandem-type siRNA expression vector. In b) stem loop-type siRNA expression vector, a short hairpin RNA is transcribed and the transcript is processed to produce siRNA.

FIG. 9 shows the effect of a dumbbell-shaped vector carrying a minimized promoter. The minimized promoter has approximately the same expression activity as wild type U6 promoter ((a)) and siRNA expressed by the minimized promoter has the ability to suppress the expression of the luciferase gene ((b)). Moreover, the minimized promoter has higher nuclear permeability than the wild type U6 promoter ((c)).

BEST MODE FOR CARRYING OUT THE INVENTION

The present invention is described below in detail in order to explain a preferred mode of the present invention which should not be construed as limiting.

1. Construction of a Dumbbell-Shaped DNA

Construction of a Template DNA Containing a Target DNA Sequence

First, a template DNA containing a target DNA sequence is prepared. Examples of the template DNA include a cDNA, a chemically synthesized DNA (either a single stranded DNA or a double stranded DNA may be used), a DNA synthesized by a biochemical method such as PCR (either a single stranded DNA or a double stranded DNA may be used). Template DNA may either be a circular-shaped DNA or a linear-shaped DNA.

The size of a target DNA sequence may be 20~2000 bases, preferably, 40~1000 bases, and more preferably, 40~500 bases. Examples of the target DNA sequence are a promoter sequence, a sequence of a target transcription region (for example, siRNA transcription sequence, a decoy transcription sequence, a non-coding RNA transcription sequence (for example, micro RNA (miRNA) transcription sequence, and tRNA transcription sequence), a sequence necessary for translation of a specific protein, and a decoy sequence. These DNA sequences can be synthesized by well known methods using a commercial DNA synthesizer and the like.

Any promoter can be used as long as it influences the efficiency of the transcription start reaction. However, polIII-type which is suitable for the expression of short RNA such as siRNA is preferred in the case where a dumbbell-shape DNA is used as the siRNA expression vector in the present invention.

Examples of the polIII-type promoter are the U6 promoter, tRNA promoter, retroviral LTR promoter, adenoviral VA1 promoter, 5S rRNA promoter, 7SK RNA promoter, 7SL RNA promoter, H1 RNA promoter, and so forth.

The names and sequences of applicable promoters are shown below.

U6 promoter
(SEQ ID NO: 1)
5'-AAGGTCGGGCAGGAAGAGGGCCTATTTCCCATGATTCCTTCATATTT

GCATATACGATACAAGGCTGTTAGAGAGATAATTAGAATTAATTTGACTG

TAAACACAAAGATATTAGTACAAAATACGTGACGTAGAAAGTAATAATTT

CTTGGGTAGTTTGCAGTTTTAAAATTATGTTTTAAAATGGACTATCATAT

GCTTACCGTAACTTGAAAGTATTTCGATTTCTTGGCTTTATATATCT

T-3'

There are several types of sequences in the wild type U6 promoter. The promoter sequence (U6 (240)) used in the later described Example 2 is as follows;

U6 (240)
(SEQ ID NO: 25)
5'-TTTCCCATGATTCCTTCATATTTGCATATACGATACAAGGCTGTTAG

AGAGATAATTAGAATTAATTTGCCTGTAAACACAAAGATATTAGTACAAA

ATACGTGACGTAGAAAGTAATAATTTCTTGGGTAGTTTGCAGTTTTAAAA

TTATGTTTTAAAATGGACTATCATATGCTTACCGTAACTTGAAAGTATTT

CGATTTCTTGGCTTTATATATCTTGTGGAAAGGACGAAACACC-3'.

H1 promoter
(SEQ ID NO: 2)
5'-AATATTTGCATGTCGCTATGTGTTCTGGGAAATCACCATAAACGTGA

AATGTCTTTGGATTTGGGAATCTTATAAGTTCTGTATGAGACCACAGATC

GATCCCC-3' tRNA promoter
(SEQ ID NO: 3)
5'-ACCGTTGGTTTCCGTAGTGTAGTGGTTATCACGTTCGCCTAACACGC

GAAAGGTCCCCGGTTCGAAACCGGGCACTACAAAAACCA-3'.

An artificial promoter in which the promoter region used for expression is minimized may be used. Examples of such artificial promoters include promoters which contain all or part of a promoter region transcribed from RNA polymerase III and which also contain at least one of the following (i)~(iv).
(i) TATA (SEQ ID NO: 26)
(i) CTTACCGTAACTTGAAAGT (SEQ ID NO: 27)
(iii) YYTCCCANNRTNCNNYGCRR (SEQ ID NO: 28)
(iv) ATGCAAAT (SEQ ID NO: 29) or its complementary sequence.
(wherein R is either guanine or adenine, Y is either cytosine or thymine, N is any one of guanine, adenine, cytosine, or thymine.)

Examples of other artificial promoters include promoters which contain all or part of a promoter region transcribed from RNA polymerase III and which also contain at least one of the following (i')~(ii')

| (i') | RRYNNARYGG |
| (ii') | GGTTCGANTCC |

(wherein R is either guanine or adenine, Y is either cytosine or thymine, N is any one of guanine, adenine, cytosine, or thymine.)

The number of bases of the artificial promoter may be 250 bases or less, preferably 150 bases or less, more preferably 100 bases or less.

Examples of artificial promoters are the U6 (90) and U6 (110) promoters described later in [Examples]. Sequences of the U6 (90) and U6 (110) promoters are as follows;

U6 (90) promoter
(SEQ ID NO: 22)
5'-TTTCCCATGATTCCTTCATATTTGCATCTTACCGTAACTTGAAAGTA

TTTCGATTTCTTGGCTTTATATATCTTGTGGAAAGGACGAAACACC-3'.

U6 (110) promoter
(SEQ ID NO: 23)
5'-TTTCCCATGATTCCTTCATATTTGCATATAGGACTATCATATGCTTA

CCGTAACTTGAAAGTATTTCGATTTCTTGGCTTTATATATCTTGTGGAA

AGGACGAAACACC-3'

Furthermore, siRNA can be expressed at a desired time using an inducible promoter. Examples of the inducible promoter are the U6 promoter inducible with tetracycline (Ohkawa, J. & Taira, K. Control of the functional activity of an antisense RNA by a tetracycline-responsive derivative of the human U6 snRNA promoter, Hum Gene Ther. 11, 577-585 (2000)) and the like. Moreover, the expression of siRNA can be induced in a tissue-specific manner by using a tissue specific promoter, or a DNA recombination system such as the Cre-LoxP system.

The number of bases of the promoter may be 1~1500 bases, preferably 40~500 bases, and more preferably 60~260 bases.

A siRNA transcriptional sequence may contain a DNA sequence encoding siRNA. Examples of target genes (mRNAs) are various disease causing genes including genetic diseases, apoptosis related genes (such as p53), leukemia gene ber-ab1 junction, genes related to cancers such as ras, myx, met, mdm2, ab1, and erbB, and genomes of pathogenic viruses such as HIV and HCV.

References which describe siRNA transcriptional sequences are as follows;

The siRNA transcriptional sequence of c-JUN is described in J Biol Chem. 2003 Jun. 27 Disruption of the c-JUN-JNK complex by a cell-permeable peptide containing the c-JUN delta domain induces apoptosis and affects a distinct set of IL-1-induced inflammatory genes. Holzberg D, Knight C G, Dittrich-Breiholz O, Schneider H, Dorrie A, Hoffmann E, Resch K, Kracht M.

The siRNA transcriptional sequence of Chk1 is described in Mol Cancer Ther. 2003 June; 2(6):543-8. Human chk 1 expression is dispensable for somatic cell death and critical for sustaining g (2) DNA damage checkpoint. Chen Z, Xiao Z, Chen J, Ng S C, Sowin T, Sham H, Rosenberg S, Fesik S, Zhang H.

The siRNA transcriptional sequence of caspase 8 is described in Proc Natl Acad Sci USA. 2003 Jun. 16 Caspase 8 small interfering RNA prevents acute liver failure in mice. Zender L, Hutker S, Liedtke C, Tillmann H L, Zender S, Mundt B, Waltemathe M, Gosling T, Flemming P, Malek N P, Trautwein C, Manns M P, Kuhnel F, Kubicka S.; Proc Natl Acad Sci USA. 2003 Jun. 16 Caspase 8 small interfering RNA prevents acute liver failure in mice. Zender L, Hutker S, Liedtke C, Tillmann H L, Zender S, Mundt B, Waltemathe M, Gosling T, Flemming P, Malek N P, Trautwein C, Manns M P, Kuhnel F, Kubicka S.

The siRNA transcriptional sequence of RECK is described in Proc Natl Sci USA. 2003 Jun. 16 Caspase 8 small interfering RNA prevents acute liver failure in mice. Zender L, Hutker S, Liedtke C, Tillmann H L, Zender S, Mundt B, Waltemathe M, Gosling T, Flemming P, Malek N P, Trautwein C, Manns M P, Kuhnel F, Kubicka S.

The siRNA transcriptional sequence of STRAD is described in EMBO J. 2003 Jun. 16; 22 (12):3062-3072. Activation of the tumor suppressor kinase LKB1 by the STE20-like pseudokinase STRAD. Baas A F, Boudeau J, Sapkota G P, Smit L, Medema R, Morrice N A, Alessi D R Clevers H C.

The siRNA transcriptional sequence of PKACα is described in J Biol Chem. 2003 Jun. 11 PKA blocks Raf-1 activity by stimulating 14-3-3 binding and blocking Raf-1 interaction with Ras. Dumaz N, Marais R.

The siRNA transcriptional sequence of PKACβ is described in J Biol Chem. 2003 Jun. 11 PKA blocks Raf-1 activity by stimulating 14-3-3 binding and blocking Raf-1 interaction with Ras. Dumaz N, Marais R.

The siRNA transcriptional sequence of Erb B3 is described in Oncogene. 2003 Jun. 5; 22 (23):3598-607. Atypical expression of ErbB3 in myeloma cells: cross-talk between ErbB3 and the interferon-alpha signaling complex. Walters D K, French J D, Arendt B K, Jelinek D F.

The siRNA transcriptional sequence of Androgen Receptor is described in Mol Endocrinol 2003 May 29 Androgen Receptor Represses the Neuroendocrine Transdifferentiation Process in Prostate Cancer Cells. Wright M E, Tsai M J, Aebersold R.

The siRNA transcriptional sequence of FADD is described in J Biol Chem 2003 May 12 cFLIP-L inhibits p38 MAPK activation: An additional anti-apoptotic mechanism in bile acid-mediated apoptosis. Grambihler A, Higuchi H, Bronk S F, Gores G J.

The siRNA transcriptional sequence of HB-EGF is described in EMBO J. 2003 May 15; 22 (10):2411-2421 TACE cleavage of proamphiregulin regulates GPCR-induced proliferation and motility of cancer cells. Gschwind A, Hart S, Fischer O M, Ullrich A.

The siRNA transcriptional sequence of TACE is described in EMBO J. 2003 May 15; 22 (10):2411-2421 TACE cleavage of proamphiregulin regulates GPCR-induced proliferation and motility of cancer cells. Gschwind A, Hart S, Fischer O M, Ullrich A.

The siRNA transcriptional sequence of p73 is described in Cancer Cell 2003 April; 3 (4) 403-10 Chemosensitivity linked to p73 function. Irwin M S, Kondo K, Marin M C, Cheng L S, Hahn W C, Kaelin W G.

The siRNA transcriptional sequence of β-catenin is described in Clin Cancer Res 2003 April; 9 (4): 1291-300 Small Interfering RNAs Directed against beta-Catenin Inhibit the in Vitro and in Vivo Growth of Colon Cancer Cells. Ve ma UN, Surabhi K M, Schmaltieg A, Becerra C, Gaynor R B.

The siRNA transcriptional sequence of APC is described in Clin Cancer Res 2003 April; 9 (4): 1291-300 Small Interfering RNAs Directed against beta-Catenin Inhibit the in Vitro and in Vivo Growth of Colon Cancer Cells. Verma U N, Surabhi R M, Schmaltieg A, Becerra C, Gaynor R B.

The siRNA transcriptional sequence of NF-κB is described in Clin Cancer Res 2003 April; 9 (4): 1291-300 Small Interfering RNAs Directed against beta-Catenin Inhibit the in Vitro and in Vivo Growth of Colon Cancer Cells, Verma U N, Surabhi R M, Schmaltieg A, Becerra C, Gaynor R B.

The siRNA transcriptional sequence of p120 is described in Gastroenterology 2003 April; 124 (4): 949-60 Up-regulation, nuclear import, and tumor growth stimulation of the adhesion protein p120 in pancreatic cancer Mayerle J, Friess H, Buchler M W, Schnekenburger J, Weiss F U, Zimmer K P, Domschke W, Lerch M M.

The siRNA transcriptional sequence of ATM is described in Cancer Res 2003 Apr. 1; 63 (7): 1550-4 Enhanced Radiation and Chemotherapy-mediated Cell Killing of Human Cancer cells by Small Inhibitory RNA Siencing of DNA Repair Factors. Collis S J, Swartz M J, Nelson W G, DeWeese T L.

The siRNA transcriptional sequence of ATR is described in Cancer Res 2003 Apr. 1; 63 (7): 1550-4 Enhanced Radiation and Chemotherapy-mediated Cell Killing of Human Cancer cells by Small Inhibitory RNA Siencing of DNA Repair Factors. Collis S J, Swartz M J, Nelson W G, DeWeese T L.

The siRNA transcriptional sequence of telomerase is described in Mol Cancer Ther 2003 March; 2 (3): 209-16 Inhibition of telomerase activity in human cancer cells by RNA interference. Kosciolek B A, Kalantidis K, Tabler M, Rowley P T.

The siRNA transcriptional sequence of cyclin G is described in Oncogene 2003 Mar. 20; 22 (11):1678-87 Modulation of p53 and p73 levels by cyclin G: implication of a negative feedback regulation. Ohtsuka T, Ryu H, Minamishima Y A, Ryo A, Lee S W.

The siRNA transcriptional sequence of MDC1 is described in Nature 2003 Feb. 27; 42 (6926); 961-6 MDC1 is a mediator of the mammalian DNA damage checkpoint. Stewart G S, Wang B, Bignell C R, Taylor A M, Elledge S J.

The siRNA transcriptional sequence of Fas is described in Nat Med 2003 Feb. 10 RNA interefenence targeting Fas protects mice from fulminant hepatitis. Song E, Lee S K, Wang J, Ince N, Ouyang N, Min J, Chen J, Shanker P, Lieberman J.

The siRNA transcriptional sequence of DNMT1 is described in Nat Genet 2002 Dec. 23 DNMT1 is required to maintain CpG methylation and aberrant gene silencing in human cancer cells. Robert M F, Morin S, Beaulieu N, Gauthier F, Chute I C, Barsalou A, MacLeod A R.

The siRNA transcriptional sequence of DNA-PKcs is described in Cancer Res 2002 Nov. 15; 62 (22); 6400-4 Silencing Expression of the Catalytic Subunit of DNA-dependent Protein Kinase by Small interfering RNA Sensitizes Human Cells for Radiation-induced Chromosome Damage, Cell killing, and Mutation. Peng Y, Zhang Q, Nagasawa H, Okayasu R, Liber H L, Bedford J S.

The siRNA transcriptional sequence of p21Cip/Waf1 is described in Gene Dev 2002 Nov. 15; 16 (22):2923-34 Cdk4 disruption renders primary mouse cells resistant to oncogene transformation, leading to Arf/p53-independent senescence. Zou X, Ray D, Aziyu A, Christov K, Boiko A D, Gudkov A V, Kiyokawa H.

The siRNA transcriptional sequence of EHZ2 is described in Nature 2002 Oct. 10; 419 (6907):624-9 The polycomb group protein EZH2 is involved in progression of prostrate cancer. Varambally S, Dhanasekaran S M, Zhou M, Barrette T R, Kunar-Sinha C, Sanda M G, Ghosh D, Pienta K J, Sewalt R G, Otte A P, Rubin M A, Chinnaiyan A M.

The siRNA transcriptional sequence of p73 is described in Oncogene 2002 Jul. 18; 21 (31), 4715-27 p53 induces the expression of its antagonist p73 Delta N, establishing an autoregulatory feedback loop. Kartasheva N N, Contente A, Lenz-Stoppler C, Roth J, Dobbelstein.

The miRNA is a small non-translated RNA which interacts with other biological molecules and influences development and differentiation. It is preferred that miRNA transcriptional sequences have DNA sequences encoding miRNAs. The miRNA transcriptional sequence is described in Kawasaki H, Taira K., Hes1 is a target of micro RNA-23 during retinoic-acid-induced neuronal differentiation of NT2 cells., Nature 2003, 423, 838-842, and other references, The number of bases of siRNA and miRNA transcriptional sequences (the promoter sequence and the sequence in the loop region are not counted, and only the region binding to a target NA is counted) may be 1200 bases, preferably 15~40 bases, and more preferably 18~25 bases.

It is preferred that tRNA transcriptional sequences have DNA sequences encoding tRNAs. The tRNA transcriptional sequences are described in Koseki S, Tanabe T, Tani K, Asano S, Shioda T, Nagai Y, Shimada T, Ohkawa J, Taira K., Factors governing the activity in vivo of ribozymes transcribed by RNA polymerase III, J. Virol. 1999 March; 73 (3): 1868-77.; Kawasaki H, Taira K. Short hairpin type of dsRNAs that are controlled by tRNA (Val) promoter significantly induce RNAi-mediated gene silencing in the cytoplasm of human cells., Nucleic Acids Res. 2003 (31), 700-707 and other references. The number of bases of tRNA transcriptional sequences may be 1~200 bases, preferably 65~110 bases, and more preferably 80~92 bases.

References presenting the necessary sequences for translation of specific proteins are as follows: The necessary sequence for translation of Bax is described in Oltvai, Z. N., Milliman, C. L. and Korsmeyer, S. J., Bcl-2 heterodimerizes in vivo with a conserved homolog, Bax, that accelerates programmed cell death, Cell 74 (4), 609-619 (1993).

The necessary sequence for translation of p53 is described in Harlow, E., Williamson, N. M., Ralston, R., Helfman, D. M. and Adams, T. E., Molecular cloning and in vitro expression of a cDNA clone for human cellular tumor antigen p53, Mol. Cell. Biol. 5 (7), 1601-1610 (1985).

The sequence necessary for translation of a specific protein may be 1~2000 bp, preferably 50~1000 bp, more preferably 65~800 bp in length.

A decoy sequence can be any sequence as long as the decoy sequence contains the same sequence as a transcription factor binding site of a gene so that, as a result, the binding of the transcription factor to the decoy sequence prevents the binding of the transcription factor to the genomic binding site, thereby suppressing the expression of the transcription factor.

One decoy sequence is as follows:

Examples of transcription factors (proteins) besides E2F to which decoy molecules are known to bind are AP-1, NF-κB, SSRE, CREB, MEF-2, CarG box, tax, VP16, TAR/tat, CRE/HRE/MRE, Heat shock RE, SRE, AP-2, sterol response element, TGF-b responsive element, HIF-1, and the like.

Decoy transcription sequences are sequences which code for decoy sequences (in the case of RNA decoys). Furthermore, decoys may be short double stranded nucleic acids (pharmaceutical agents) including the sequence of a DNA binding site of a transcription factor. In the latter case, a dumbbell-shaped DNA itself functions as a decoy without being transcribed.

The cDNA which contains a target DNA sequence can be constructed by incorporated the target DNA into plasmids, viruses, PCR products, and the like. The method for incorporating is described in references such as Molecular Cloning by J. Sambrook and D. W. Russell (www.MolecularCloning.com).

The method for chemical synthesis of a template DNA which contains a target DNA sequence can be performed by well known methods.

Amplification of Nucleic Acid

A target DNA sequence in a template DNA is amplified (1 in FIG. 1) by PCR using sense and antisense primers. Herein, each of the sense and antisense primers contains the following sequence (a) at the 5' end and contains the following sequences (b), (c), and (d) in order from the 5' end to the 3' end.

(a) a part of a sense sequence of a nickase recognition sequence, comprising the sequence of a region between the site where a nick is introduced by the action of a nickase and the 3' end.

(b) a sequence capable of forming a loop structure from a single strand.

(c) the entire antisense sequence of the nickase recognition sequence (a).

(d) a sequence complementary to all or part of the sequence of the target DNA.

The number of bases of sequence (a) may be 1~10 bases, preferably 1~7 bases, more preferably 5 bases.

The number of bases of sequence (b) may be 1~50 bases, preferably 1~10 bases, more preferably 3~6 bases.

The number of bases of sequence (c) may be 4~20 bases, preferably 5~15 bases, more preferably 7~10 bases.

The number of bases of sequence (d) may be 5~50 bases, preferably 10~30 bases, more preferably 15~25 bases.

Nickases which create a nick in only one strand of a double stranded DNA are preferred. Nickases which create a nick in only one strand of a double stranded DNA and their recognition sequences (restriction enzyme sites) are listed below. These nickases are commercially available at the present time.

The sequences listed below are sequences of the strand (in this case, [sense sequence of the nickase recognition sequence]) which are recognized by nickases to have a nick introduced therein.

Bpu10I restriction enzyme site: GCTNAGG (N. Bpu10I nickase recognizes GC'TNAGG sequence and creates a nick at the ' position; N can be any one of A, T, G, or C).

N.BpvC IB recognition site: CCTCAGC (N.BpvC IB nickase recognizes CC'TCAGC sequence and creates a nick at the ' position).

N.BstNBI recognition site: GACTCNNNNN (N.BstNB I nickase recognizes GAGTCNNNN'N sequence and creates a nick at the ' position).

N.Alw I recognition site: GGATCNNNNN (N.Alw I nickase recognizes GGATCNNNN'N sequence and creates a nick at the ' position).

N.BpvC IA recognition site: GCTGAGG (N.BpvC IA nickase recognizes GC'TGAGG sequence and creates a nick at the ' position).

In the case the nickase is N.Bpu10I, TNAGG and CCTNAGC may be used as sequences (a) and (c), respectively.

In the case the nickase is N.BpvC IB, TCAGG and GCTGAGC may be used as sequences (a) and (c), respectively.

In the case the nickase is N.BstNB I, N and NNNNNGACTC may be used as sequences (a) and (c), respectively.

In the case the nickase is N.Alw I, N and NNNNNGATCC may be used as sequences (a) and (c), respectively.

In the ease the nickase is N.BpvC IA, TGAGG and CCTCAGC may be used as sequences (a) and (c), respectively.

The sequence (b) can be any sequence as long as its single strand is capable of forming a loop structure. One example is shown below:

(T)n (wherein n is at least one, preferably 1~10, more preferably 3~6).

The sequence (b) may be an aptamer DNA. A aptamer DNA sequence is as follows;

An aptamer for thrombin; GGNTGGN$_{2-5}$GGNTGG (SEQ ID NOS: 4~7).

A sequence motif of a DNA aptamer which binds to a dye (Reactive Green 19); forms a single-stranded loop. 5'-GGCGTTCGGGGGGTA-3' (SEQ ID NO: 8)

For example, the sequence (b) in either a sense or an antisense primer can be an aptamer DNA and the sequence (b) in the other primer can be modified by a dye (for example, Eu$^{3+}$ complex (a complex compound consisting of a rare-earth dye such as europium and an organic compound), Reactive Green 19 and the like). In the case where an Eu$^{3+}$ complex dye-dumbbell-shaped DNA is transfected into cells while the fused protein consisting of DNA aptamer binding motif of thrombin and a target protein is expressed, the target protein is, as a result, labeled with the (rare-earth based) dye. Thus, applications such as a highly sensitive detection of target proteins by delayed fluorescence in cells become possible. A dumbbell-shaped DNA can be constructed with the sequence (b) in either a sense or an antisense primer as a sequence of an aptamer DNA and the sequence (b) in the other primer being modified with a dye. The dumbbell-shaped DNA can be easily transfected into cells after attaching peptides or proteins in vitro and/or in vivo which specifically recognize an aptamer DNA.

The sense primer and/or the antisense primer may further contain a first spacer sequence and a second spacer sequence. Herein, the first spacer sequence and the second spacer sequence are complementary to each other, and the first and second spacer sequences are connected so that they are in opposite directions to each other with the sequence (b) interposed.

An example of the first spacer may be AG and an example of the second spacer may be TC.

It is preferred that the sense and antisense primers contain TN$^1$AGG (wherein T, A, and G represent thymine, adenine, and guanine, respectively, and N$^1$ represents any one of adenine, cytosine, guanine, or thymine) in the sequence (a), (T)n (wherein T represents thymine and n is an integer of at least one) in the sequence (b), and CCTN$^{11}$AGC (wherein C, T, A, and G represent cytosine, thymine, adenine, and guanine, respectively, and N$^1$ represents any one of adenine, cytosine, guanine, or thymine) in the sequence (c) when N.Bpu10I is used as a nickase. The symbol n in (T)n represents an integer of at least one, preferably an integer between 1 and 10 and, more preferably an integer of any one of 3~6. Sense and antisense primers may further contain a first and a second spacer sequence, wherein the first spacer sequence is represented by AG and the second spacer sequence by TC in the sense primer. The first spacer sequence may be represented by TC and the second spacer sequence by AG in the antisense primer. In the sense and antisense primers, the first and second spacers may be connected so that they are in an opposite directions to each other with sequence (b) interposed.

The sequence (d) contains a sequence complementary to all or part of a region of the 5' end of a sense strand of a target DNA sequence in the sense primer.

The sequence (d) contains a sequence complementary to all or part of a region of the 5, end of an antisense strand of a target DNA sequence in the antisense primer.

The sense and antisense primers may be 10~200 bp, preferably 20~150 bp, more preferably 30~120 bp in length.

Furthermore, in the sense primer and/or antisense primer, at least one position of the nucleic acid backbone or bases of sequence (b) and/or the spacer sequence may be modified by a functional group.

It is advantageous to create these modifications because these modifications provide a reactive site where delivery agents and the like can be attached to a dumbbell-shaped DNA constructed using these primers. Examples of modifications include modifications by functional groups such as an amino group, a fluorescent group such as fluorescein, and a biotin group, and attachment of delivery agents such as proteins, proteins derived from viruses, glycoproteins, ferritin, lectin family, low-density lipoprotein (LDL), antibodies, artificial antibodies, peptides, peptide mimics, insulin, polyethylene glycol, amino acids, non-natural amino acids, co-polymers of amino acids and non-natural amino acids, biotin, retinol, retinol derivatives, sugar, oligosaccharides, cholesterol, estradiol, estrone, cholesterol derivatives, steroids, hormones, steroid derivatives, fats, vitamins, and folic acid.

Multiple modifications can be also made using different functional groups and delivery agents. The attached functional groups may be used to add or substitute other functional groups, functional peptides including TAT and NLS, cancer cell specific antibodies, fluorescent or phosphorescent dyes which have an ability to donate electrons, fluorescent or phosphorescent dyes which have an ability to accept electrons, and delivery agents such as proteins, proteins derived from viruses, glycoproteins, ferritin, lectin family, low-density lipoprotein (LDL), antibodies, artificial antibodies, peptides, peptide mimics, insulin, polyethylene glycol, amino acids, non-natural amino acids, co-polymers of amino acids and non-natural amino acids, biotin, retinol, retinol derivatives, sugar, oligosaccharides, cholesterol, estradiol, estrone, cholesterol derivatives, steroids, hormones, steroid derivatives, fats, vitamins, and folic acid.

Sense and antisense primers may be phosphorylated at the 5' end. If the sense and antisense primers are phosphorylated at the 5' end, a hairpin loop-structured DNA is circularized by intramolecular ligation when it is reacted with DNA ligase in the last step of dumbbell-shaped DNA construction. Phosphorylation of the 5' end can be performed by reacting with a phosphorylation reagent followed by ammonia treatment for deprotection in the last step of DNA autosynthesis. In the case of chemically synthesized oligo DNA (the 5' end is a hydroxyl group), phosphorylation can be performed enzymatically using T4 DNA ligase.

In case the 5' end of sense and antisense primers are not phosphorylated, then it is recommended that DNA as an amplification product obtained by a nucleic acid amplification method using these primers should be phosphorylated at the 5' end in any one of the steps that precede the treatment with DNA ligase (for example, after PCR, after nickase treatment, after heat treatment, or after annealing).

A target DNA sequence in a template DNA can be amplified by well known nucleic acid amplification methods using sense and antisense primers. For example, a template DNA is mixed with sense and antisense primers followed by PCR using DNA polymerase.

Conversion of a Linear-Shaped DNA to a Dumbbell-Shaped DNA

An amplified linear-shaped DNA product is mixed with a nickase (for example, 1 μg of DNA is mixed with 0.5~2 U of a nickase) and the reaction mixture is incubated (for example, at 25~50° C. overnight). This procedure introduces a nick in only one strand of the amplified linear-shaped DNA product (a double stranded DNA) (arrows in 2a-c in FIG. 1).

Then, the reaction mixture is heated (for example, at 90~100° C. for 0.5~10 min) and cooled to room temperature over 1 min~2 hours (annealing). A hairpin loop structure is formed at the ends of the amplified linear-shaped DNA product by these procedures (3a~c in FIG. 1).

DNA ligase (for example, 1 μg of DNA is mixed with 175~1000 U of DNA ligase) and ligation buffer are added to the mixture and the resulting mixture is incubated (for example, at 14~37° C. for 3 min~6 hours). A dumbbell-shaped structure is formed by intramolecular ligation reaction within the hairpin loop structure by these procedures.

The above described conversion process is a one-pot reaction. That is, the conversion process can be performed within a microtube.

The size of a dumbbell-shaped DNA is 12~2000 bases (equivalent to a double strand), preferably 50~1000 bases (equivalent to a double strand), more preferably 150~600 bases (equivalent to a double strand).

The product recovered after the ligation may be purified by known methods.

A dumbbell-shaped DNA is constructed by the procedures described above. The dumbbell-shaped DNA may be a modified DNA produced from an optically active boranophosphate. The method to produce a modified DNA from boranophosphate is described in Nucleic Acids Research, 1997, Vol. 25, No. 8, 1611-1617.

2. Assessment of the Stability of a Dumbbell-Shaped DNA Against Digestion Reaction by Exonuclease The dumbbell-shaped DNA constructed in 1 is treated with exonuclease at 25~42° C. for 10 min~2 hours. Small amounts of dumbbell-shaped DNA are collected before and after the exonuclease treatment and subjected to electrophoresis and bands are visualized. Results show that the dumbbell-shaped DNA is resistant to digestion reaction by exonuclease.

3. Site Specific Modification of a Dumbbell-Shape DNA

The dumbbell-shaped DNA constructed in 1 can be site specifically modified by known methods. For example, the dumbbell-shaped DNA can be modified with fluorescein at the site of amino group attachment by using a commercial Amine Labeling Kit (Panvera, Madison, Wis.) if the amino group is attached to a face present at a specific site (for example, a base in the sequence forming a loop structure by a single strand). Furthermore, if a SH group is attached to unmodified primer DNA using a commercial kit (Fast Tag®, Vector Laboratories Co.), it can be reacted with various maleimide derivatives.

4. Attachment of Delivery Agents to a Dumbbell-Shaped DNA

The dumbbell-shaped DNA constructed in 1 may have delivery agents attached thereto by known methods.

Examples of delivery agents are proteins, proteins derived from viruses, glycoproteins, ferritin, lectin family, low-density lipoprotein (LDL), antibodies, artificial antibodies, peptides, peptide mimics, insulin, polyethylene glycol, amino acids, non-natural amino acids, co-polymers of amino acids and non-natural amino acids, biotin, retinol, retinol derivatives, sugar, oligosaccharides, cholesterol, estradiol, estrone, cholesterol derivatives, steroids, hormones, steroid derivatives, fats, vitamins, and folic acid.

Examples of methods of attaching delivery agents to the dumbbell-shaped DNA are described below.

In the first example, an amide group (—$NH_2$) is introduced into the dumbbell-shaped DNA (a dumbbell-shaped DNA-$NH_2$) and then the product is reacted with EMCS (6-maleimidohexanoic acid N-hydroxysuccinimide ester) to maleimidate the dumbbell-shaped DNA (a dumbbell-shaped DNA-NHCO-maleimide). Peptides can be attached to the dumbbell-shaped DNA by reacting the maleimidated dumbbell-shaped DNA (dumbbell-shaped DNA-NHCO-maleimide) with a SH group contained in peptides and the like (a dumbbell-shaped DNA-NHCO-peptide).

In the second example, an amide group (—$NH_2$) is introduced into the dumbbell-shaped DNA (a dumbbell-shaped DNA-$NH_2$) and then the product is reacted with a succinimide ester derivative to produce a modified form of the dumbbell-shaped DNA (a dumbbell shaped-DNA-NHCO— derivative).

5. Application of a Dumbbell-Shaped DNA

A dumbbell-shaped DNA can be used as a DNA vector. Transfection of a DNA vector into cells is conducted by known methods. For example, a method of transfecting mammalian cells can be chosen from the calcium phosphate method (Virology, Vol. 52, p. 456 (1973)), an electroporation method (Nucleic Acids Res., Vol. 15, p. 1311 (1987)), lipofection method (J. Clin. Biochem. Nutr., Vol. 7, p. 175 (1989)), infectious transfection by viruses (Sci. Am., p. 34, March (1994)), a gene gun method, and the like. Methods of transfection into plant cells include an electroporation method (Nature, Vol. 319, p791 (1986)), a polyethelene glycol method (EMBO J., Vol. 3, p. 2717 (1984)), a particle gun method (Proc. Natl. Acid. Sci. USA, Vol. 85, p. 8502 (1988)), an *Agrobacterium* mediated method (Nucleic Acids Res., Vol. 12, p. 8711 (1984)), and the like.

Cells transfected with a DNA vector are selected by known methods, such as PCR and hybridization, using a DNA sequence which is specific to the DNA vector as a probe or a primer. In case the DNA vector contains a selectable marker, a phenotype due to the selectable marker can be used as an indicator for selection.

In case the dumbbell-shaped DNA or the delivery agent attached dumbbell-shaped DNA contains a siRNA transcriptional sequence, the expression of the siRNA targeted gene (mRNA) can be suppressed. Therefore, it can be applied as a pharmaceutical agent for disease prevention and/or treatment or reagents for analyzing gene function. For example, in case siRNA targeted genes are causative genes for various diseases including genetic diseases, apoptosis related genes (for example, p53), leukemia gene bcr-abl junction, genes related to cancers such as ras, myx, met, mdm2, ab1, and erbB, genomes of pathogenic viruses such as HIV and HCV, the dumbbell-shaped DNA or the delivery agent attached dumbbell-shaped DNA can be administered to humans and other animals as pharmaceutical agents to prevent and/or treat diseases.

By transfecting the dumbbell-shaped DNA which contains siRNA sequence or the delivery agent attached dumbbell-shaped DNA into tissues or cells of patients, the expression of a target gene in cells can be suppressed. Transfection of a dumbbell-shaped DNA or a delivery agent attached dumbbell-shaped DNA can be performed by various methods such as, for example, transfecting DNAs into cells using liposomes which contain these DNAs ("Lipidic vector system for gene transfer" (1997) R. J. Lee and L. Huang. Crit. Rev. Ther. Drug Carrier Syst 14, 173-206; Nakanishi et al., Protein. Nucleic acid, Enzyme Vol. 44, No. 11, 1590-1596 (1999)), a calcium phosphat method, an electroporation method, a lipofection method, a micro injection method, and a gene gun method. Transfection of a dumbbell-shaped DNA or a delivery agent attached dumbbell-shaped DNA into cells can be also performed by, for example, removing part of cells from a diseased area, transfecting the gene into the cells in vitro, and replacing the cells back into tissues. Alternatively, the DNAs may be transfected into tissues in the diseased area.

Pharmaceutical compositions which contain a dumbbell-shaped DNA or a delivery agent attached dumbbell-shaped DNA as active ingredients can contain pharmaceutically acceptable carriers (for example, diluents such as physiological saline and buffer) as necessary. Depending on the seriousness of the disease, the patients' condition, and patients' response to the drugs, administration may be continued until the treatment effect or an improvement in disease condition is observed using proper dosage, proper administration methods, and proper frequency.

Functional nucleic acids such as siRNAs, double stranded RNAs including hairpin RNAs, ribozymes, and antisense RNAs can be expressed in cells or tissues or expression of the genes can be suppressed using the dumbbell-shaped DNA in the present invention. Targets of the functional nucleic acids are preferably viruses such as HIV, HCV, or HBV or cancer genes. The dumbbell-shaped DNA of the present invention can be used as DNAzyme if it can suppress the expression of genes when it is transfected into cells or tissues.

Compositions containing the dumbbell-shaped DNA of the present invention can be applied for various uses such as pharmaceutical agents, cosmetics, reagents, and foods.

6. Primer Compositions and Kits

Other uses provided by the present invention include a kit containing at least one pair primers consisting of the sense and antisense primers described above. This kit can be used to construct a dumbbell-shaped DNA. The kit may contain components other than at least one pair of primers consisting of the sense and antisense primers described above. For example, the kit may contain a template DNA for nucleic acid amplification, DNA polymerase, dNTPs of various bases, nickase, DNA ligase, buffer (for example, Tris-buffer, phosphate buffer, and cacodylic acid buffer), a manual which explains the use of the kit, cobalt salt, magnesium salt, manganese salt, chemicals necessary for further attachment of functional groups (maleimide derivatives, succinimide ester derivatives, functional peptides, and proteins and antibodies which have active sites).

EXAMPLES

The present invention is described in detail below with reference to Examples. However, these Examples are for explanation of the present invention, and should not be construed as limiting.

Example 1

Experimental Protocol

All of the solverts and reagents were purchased and were not further purified in this experiment. Assays were performed at least three times.
Plasmid Construction Plasmids pU6i-EGFP and pU6i-lamin contained U6 promoter and hairpin-type siRNA expression sequences for enhanced green fluorescent protein (EGFP) and lamin, respectively.

These plasmids were constructed as follows: First, the present inventors constructed siRNA expression vectors based on a commercial pU6icassette vector (iGENE Therapeutics, Tsukuba, Japan). This commercial vector contains a human U6 promoter and two BspM1 sites. The present inventors synthesized oligonucleotides (by outsourcing) which contained a hairpin sequence, a terminator sequence, and an overhang sequence to construct an siRNA expression vector.

Then, these fragments were annealed and inserted (ligation) at a BspMI site of the pU6i cassette vector described above.

The inserted sequence just after the U6 promoter was as follows:

pU6i-EGFP;
(SEQ ID NO: 9)
5'-GGCTATGTCTAGGAGTGTACCTAGAATTACATCAAGGGAGATGGTGC

GCTCCTGGACGTAGCC-3'.

pU6i-lamin;
(SEQ ID NO: 10)
5'-GGGTAATTGGTAGATTAAGCGGTGTGCTGTCCCGCTTGATCTGCCAA

TTGCCC-3'.

Conventional Method of Constructing a Dumbbell-Shaped DNA Intermolecularly Using 3 Independent Oligonucleotides
(a) PCR Amplification of a Linear-Shaped DNA Encoding siRNA that is Generated under the Control of the U6 Promoter:

PCR reaction was performed by mixing 500 pmol of each synthesized DNA primer with pU6i-lamin vector and Ex Taq™ DNA polymerase (TaKaRa, Shiga, Japan). Sequences of the sense and antisense strands of primers for PCR were, 5'-pGGGAATTCACCTGCCGGCGAGGGTTTTCCC AGTCACGACGTTG-3'(SEQ ID NO: 11) and 5'-pGGCTG-CAGACCTGCCGGCCACCG AGCG GATAACAATTTCA CACAGG-3'(SEQ ID NO: 12). Both primers contained BspMI recognition sequences (underlined) and their 5' ends were phosphorylated. PCR products were purified using Wizard® SV Gel and PCR Clean-Up System (Promega, Madison, Wis., USA) and digested with BspMI. Digestion was performed for 7 hours at 37° C. and the product was isolated using Wizard® SV Gel and PCR Clean-Up System (Promega).

(b) Conversion of a Linear-Shaped DNA for siRNA Expression into a Dumbbell-Shaped DNA:

PCR products which were not dumbbell-shaped were converted into a dumbbell-shape using T4 DNA ligase (DNA ligation kit; TaKaRa) by reacting with 10-fold equivalent excess of oligonucleotide-cap molecules. A hairpin-structured DNA of oligonucleotide-cap which contained a cohesive 5' end was obtained before the ligation reaction by heating at 95° C. for 1 min. and gradually cooling to room temperature over one hour.

Sequences of the oligonucleotide-cap were 5'-pGGTGT-GTCCGCGTTGGCTTTTGCCAA CGCGGACA-3' (SEQ ID NO: 13) and 5'-pCCTCGGCCTATAGTGAGTCG-TATTAG GCGGGAACCGCCTAATACGACTCACTAT-AGGCC-3' (SEQ ID NO: 14). The reaction mixture was incubated at 16° C. overnight and the ligation products were obtained by phenol/chloroform extraction followed by ethanol precipitation.

A novel method of producing a dumbbell-shaped DNA vector by intramolecular ligation of PCR products.

(1) PCR Amplification of a Linear-Shaped DNA Encoding siRNA Against Lamin that is Generated Under the Control of the U6 Promoter:

PCR reaction was performed by mixing 500 pmol of each synthesized DNA primer with pU6i-lamin vector and Ex Taq™ DNA polymerase (TaKaRa, Shiga, Japan). Sequences of the sense and antisense strands of the common primers for PCR were 5'-pTTAGGAGTT X"TCTCCTAAGCGTTTT CCCAGTCACGACGTTG-3' (n=1~3) (SEQ ID NOS: 15~17) and 5'-pTTAGGTCTTTTGA CCTAAGCGAGCGGATAACAATTTCACACAGG-3' (SEQ ID NO: 18). Both primers contained N.Bpu10I recognition sequences (underlined) and the 5' ends were phosphorylated. PCR products were purified using Wizard® SV Gel and PCR Clean-Up System (Promega, Madison, Wis., USA). The sense primer contained deoxythymidine which was unmodified ($X^1$; dT), modified with an amino group ($X^2$, amino-modified dT), or modified with fluorescein ($X^3$, fluorescein-modified dT). These HPLC purified common primers were purchased from Hokkaido System Science Co., Ltd. (Sapporo, Japan).

(2) PCR Amplification of a Linear-Shaped DNA Encoding siRNA Against EGFP that is Generated Under the Control of the U6 Promoter:

The first PCR reaction was performed by mixing 500 pmol of each synthesized DNA primer with pU6i-EGFP plasmid DNA and Ex Taq™ DNA polymerase (TaKaRa, Shiga, Japan). The sense and antisense strands of the primers for the first PCR were 5'-GTTTTCCCAGTCACGACGTTGAAGG TCGGGCAGGAAGAG-3' (SEQ ID NO: 19) and 5'-GAC-CGGATAACAATTTCACACAGGAA AAAGGCTACGTC-CAGGAG-3' (SEQ ID NO: 20). The first PCR product was purified by 8% polyacrylamide gel electrophoresis. The second PCR reaction was performed using common primers and the isolated PCR fragment as a template DNA under the same conditions. The second PCR product was purified using Wizard® SV Gel and PCR Clean-Up System (Promega, Madison, Wis., USA).

Base sequence of a liner-shaped DNA encoding siRNA was as follows:

```
                                       (SEQ ID NO: 21)
TTAGGAGTTTTCTCCTAAGCGTTTTCCCAGTCACGACGTTGAAGGTCGGG

CAGGAAGAGGGCCTATTTTCCATGATTCCTTCATATTTGCATATACGATA

CAAGGCTGTTAGAGAGATAATTAGAATTAATTTGACTGTAAACACAAAGA

TATTAGTACAAAATACGTGACGTAGAAAGTAATAATTTCTTGGGTAGTTT

GCAGTTTTAAAATTATGTTTTAAAATGGACTATCATATGCTTACCGTAAC

TTGAAAGTATTTCGATTTCTTGGCTTTATATATCTTGTGGAAAGGACGAA

ACACCGGCTATGTCTAGGAGTGTACCTAGAATTACATCAAGGGAGATGGT

GCGCTCCTGGACGTAGCCTTTTTCCTGTGTGAAATTGTTATCCGCTCGCT

TAGGTCAAAAGACCTAA.
```

(3) Conversion of a Linear-Shaped DNA into a Dumbbell-Shaped DNA for siRNA Expression:

Each linear-shaped PCR product (18.8 µg) was mixed with 18.8 U of N.Bpu10I (MBI Fermentas, Hanover, Md.) and incubated at 37° C. overnight. The reaction mixture was heated at 95° C. for 1 min. and then gradually cooled to room temperature over one hour. This step introduced a hairpin loop structure at the ends. T4 DNA ligase (15,750 U) and ligation buffer (TaKaRa) were directly added to the reaction mixture and incubated at 16° C. for 3 hours for intramolecular ligation at the end of hairpin structure. It is significant that the conversion method described above is a one-pot reaction. That is, all of the reactions can be conducted within one microtube. Ligated products were obtained by phenol/chloroform extraction followed by ethanol precipitation. Assessment of vector stability against exonuclease digestion in vitro The stability of the linear and dumbbell-shaped vectors was assessed by digesting them with exonuclease III (1500 U/µg of DNA, TaKaRa) at 37° C. for 1 hour. Aliquots of each fraction before and after digestion reaction were analyzed by 8% polyacrylamide gel electrophoresis. Gels were analyzed after electrophoresis by a FluorImager 595 (Molecular Dynamics, Uppsala, Sweden). This apparatus had an Argon laser (488 nm) as an exciting light source and a colored filter (around 530 nm) was used to detect fluorescence of fluorescein ($\lambda_{max}$=492 nm). Ethidium bromide staining of the above described gel was conducted. The quantity of DNA and the presence of attached fluorescein were analyzed by quantifying the bands in the gel using NIH Image program and ImageQuant program (Molecular Dynamics). The intensity of each band was quantified by a standard curve using a standard sample and the efficiency of convention from the linear-shaped DNA to the dumbbell-shaped DNA was determined.

Site Specific Modification of a Dumbbell-Shaped Vector by Fluorescein

Fluorescein Amine Labeling Kit (Panvera, Madison, Wis.) was used according to the manual to chemically modify the dumbbell-shaped vector. A short summary is as follows;

67 nM of the dumbbell-shaped vector (30 µl containing 100 mM phosphate buffer (pH 7.0) solution, 4 mM succinimide ester of fluorescein) was incubated at 37° C. for 1 hour. The reaction was then stopped by the addition of 100 mM Tris/HCl buffer (pH 8.0). The reaction mixture was left in the buffer for 30 min. DNA was isolated by Wizard® SV Gel and PCR Clean-Up System (Promega, Madison, Wis., USA).

Cells, Cell Culture, Transfection, and GFP Fluorescent Assay.

Hela S3/EGFP cells were obtained as follows; Hela S3 cells were transfected with a linearized pHygEGFP (Clontech, East Meadow Circle, Pa.) and hygromycin resistant clones were selected. Cell culture was performed using Dulbecco's modified Eagle's medium (DMEM; Sigma, St. Louis, Mo.) supplemented with 10% (v/v) heat-inactivated fetal bovine serum (FBS; GIBCO-BRL, Gaithersburg, Md.), hygromycin (100 μg/ml; Sigma), and antibiotic-antimycotic mixture (GIBCO-BRL). One of the clones, that is, HeLa S3/EGFP clone #3 was used in the following experiments. Cells were maintained in the above described media at 37° C. in a 5% $CO_2$ incubator. Cells were cultured until they were approximately 40~50% confluent in an 8-well chambered glass slide (Nalge Nunc International, Naperville, Ill.) and transfected with DNA. Transfection was performed using OPTI-MEM media (Invitrogen, Carlsbad, Calif.) and Trans-It LT-1 reagent (PanVera, Madison, Wis.) according to the manual supplied with the reagents. Cells were transfected individually with 100 ng each of the dumbbell-shaped vector that would express siRNA targeted against EGFP gene, the linear-shaped PCR product vector, or the pU6i-EGFP plasmid vector. Mock transfection was performed as a control experiment by transfecting cells with only transfection reagents. Cells were incubated for 48 hours after transfection. The culture media was replaced with fresh medium at 24 hours after transfection. Live cells in the glass slide were observed after 48 hours using a fluorescence microscope (LSM-510, Carl Zeiss, Oberkochen, Germany).

Results and Discussion

Synthesis

Key steps in constructing a dumbbell are shown in FIG. 1. There are 3 steps involved in the reaction.

N.Bpu101 is a site and strand specific endonuclease created artificially by engineering methods. It creates a nick in only one strand of a double stranded DNA.

As shown in FIG. 1, nickase in step 2 creates a nick in only one strand of DNA.

It should be emphasized that the efficiency of circularization was 90%. This is because the circularization is due to the process of an intramolecular ligation reaction.

A compound in which a primary amino group was attached at a specific site to a dumbbell-shaped DNA was successfully converted into a fluorescent dumbbell DNA using succinimide ester. In contrast, a dumbbell without a primary amino group did not react with succinimide ester at all.

This result indicates that various substituents can be site specifically attached to the hairpin loop region of a dumbbell-shaped DNA.

A fluorescent dumbbell-shaped DNA could also constructed by synthesis using fluorescent primers. A dumbbell-shaped DNA has a hairpin oligonucleotide structure at both ends; therefore, it is known to be resistant to exonuclease digestion. The intermediate 2c and dumbbell 4d were treated with exonuclease separately for 1 hour and analyzed by 8% PAGE.

As the result in FIG. 2 indicates, DNA containing free ends was completely digested by 1 hour of exonuclease treatment, however, the dumbbell clearly showed resistance to digestion.

Cell Assay

A plasmid, linear-shaped DNA, and dumbbell DNA all contained the same expression cassette. The cassette contained both the U6 promoter and the gene for expression of siRNA targeted against EGFP. The present inventors transfected these different siRNA expression vectors into Hela/EGFP in order to assess the suppression effect of the target mRNA gene in cells.

Specific and effective down regulation of the target was confirmed when DNA expressing siRNA targeted against EGFP was used.

Reproducibility was confirmed three times.

The present inventors confirmed that the highest and most reproducible suppression occurred when a dumbbell DNA was used.

The present inventors discovered that a dumbbell siRNA expression vector was more effective than a linear-shaped PCR product after 48 hours of incubation under these conditions.

That is, the RNAi effect induced by a dumbbell DNA was more superior and the effect lasted longer than those by a linear DNA.

The present inventors believe that the lifetime of a dumbbell DNA inside of cells is longer than that of a linear-shaped DNA and this explains why RNAi effect by a linear-shaped DNA decreases after 48 hours. As is shown in the in vitro experiment using exonuclease described previously, it is considered that the dumbbell DNA is more stable against exonuclease than the linear-shaped DNA in cells.

Example 2

The minimum expression-type DNA unit which can be constructed by a dumbbell-shaped DNA consists of a sequence (promoter) recognized by RNA polymerase and a sequence coding for the RNA to be expressed. It is preferred that DNAs to be transferred into cells are as short as possible when considering the cost of pharmaceutical agents and transfection efficiency. Therefore, it is very beneficial to transfect the shortest possible DNAs if functional analysis of a gene and gene therapy are considered.

Construction and Analysis of a Minimized Promoter

Minimized promoters, the U6 (90) and U6 (110) promoters, were constructed for comparison with wild type promoter. Both promoters are less than half the length of the wild type U6 promoter. Vectors were constructed by connecting a DNA sequence coding for siRNA targeted against luciferase down stream of the minimized promoter.

Chemically synthesized DNAs possessing U6 (90) promoter sequence or U6 (110) promoter sequence were amplified by PCR, digested with EcoRI and BspMI and then cloned into a piGENE-hU6 vector (iGENE Therapeutics, Tsukuba, Japan) to insert promoter DNA. The plasmid containing the promoter sequence was digested with BspMI and then the DNA sequence 5'-GCAGAAGCTATGAAACGATTTGCT-TCCTGTCACAAATCGTTCATAGCTTCTGCTTTTT-3' (SEQ ID NO: 24) coding for siRNA targeted against luciferase gene was inserted to construct an siRNA expression plasmid. RNA expression level was quantified by Northern Blot method after transfection of the vector DNA into HeLa cells. Furthermore, luciferase luminescence was measured to compare siRNA effects.

A vector DNA was subjected to PCR using a primer containing fluorescein dye, followed by incubation with digitonin treated HeLa cells. Fluorescence was measured after 1 hour.

Results and Discussion

Expression level was measured in the U6 (90), U6 (110), and wild type 136 promoter systems. Minimized promoters had approximately the same expression activity as wild type U6 promoter (FIG. 9(a)). Moreover, siRNA expressed from minimized promoters were able to suppress the expression of the luciferase gene (FIG. 9(b)). Furthermore, it was clear that a minimized vector had higher nuclear permeability than a conventional vector, when the cell nucleus permeability of a DNA vector labeled with fluorescent dye was examined (FIG. 9(c)).

All published materials, patents, and patent applications cited in the present description are incorporated herein by reference.

INDUSTRIAL APPLICABILITY

A dumbbell-shaped DNA in the present invention can be useful for gene therapy

Sequence List Free Text

SEQ ID NO: 1 shows the base sequence of the U6 promoter.

SEQ ID NO: 2 shows the base sequence of the H1 promoter.

SEQ ID NO: 3 shows the base sequence of the tRNA promoter.

SEQ ID NO: 4 shows the base sequence of an aptamer for thrombin.

SEQ ID NO: 5 shows the base sequence of an aptamer for thrombin.

SEQ ID NO: 6 shows the base sequence of an aptamer for thrombin.

SEQ ID NO: 7 shows the base sequence of an aptamer for thrombin.

SEQ ID NO: 8 shows the base sequence of an aptamer which binds to Reactive Green 19.

SEQ ID NO: 9 shows the base sequence of the insertion sequence just after the U6 promoter in U61-EGFP.

SEQ ID NO: 10 shows the base sequence of the insertion sequence just after the U6 promoter in pU6i-lamin SEQ ID NO: 11 shows the base sequence of the sense strand of the primer for PCR.

SEQ ID NO: 12 shows the base sequence of the antisense strand of primer for PCR.

SEQ ID NO: 13 shows the base sequence of an oligonucleotide-cap.

SEQ ID NO: 14 shows the base sequence of an oligonucleotide-cap.

SEQ ID NO: 15 shows the base sequence of the sense strand of a common primer for PCR.

SEQ ID NO: 16 shows the base sequence of the sense strand of a common primer for PCR SEQ ID NO: 17 shows the base sequence of the sense strand of a common primer for PCR SEQ ID NO: 18 shows the base sequence of the antisense strand of a common primer for PCR.

SEQ ID NO: 19 shows the base sequence of the sense strand of a primer for PCR

SEQ ID NO: 20 shows the base sequence of the antisense strand of the primer for PCR SEQ ID NO: 21 shows the base sequence of a linear-shaped DNA coding for siRNA.

SEQ ID NO: 22 shows the base sequence of the U6 (90) promoter.

SEQ ID NO: 23 shows the base sequence of the U6 (110) promoter.

SEQ ID NO: 24 shows the DNA sequence coding for siRNA targeted against the luciferase gene.

SEQ ID NO: 25 shows the base sequence of the U6 (240) promoter (wild type U6 promoter).

The invention claimed is:

1. A method for producing a dumbbell-shaped DNA, wherein each of sense and antisense strands is connected at both the 5' and 3' ends of a linear-shaped double stranded DNA by a single stranded DNA loop structure, comprising the steps of:
1) amplifying a target DNA in a template DNA by PCR using sense and antisense primers attached to the target DNA, wherein each of the sense and antisense primers contains the following sequence (a) at the 5' end and also contains the following sequences (b), (c), and (d) in order from the 5' end to the 3' end, (a) a part of a sense sequence of a nickase recognition sequence, comprising the sequence of a region between the site where a nick is introduced by the action of a nickase, and the 3' end, (b) a sequence capable of forming a loop structure from a single strand, (c) the entire antisense sequence of the nickase recognition sequence (a), (d) a sequence complementary to all or part of the sequence of the target DNA;
2) treating the amplified DNA product of step 1) with a nickase of (a);
3) heating and then annealing the nickase treated amplified DNA product of step 2); and
4) treating the heated and annealed amplified DNA product of step 3) with DNA ligase, wherein the sense and antisense primers used in step 1) are phosphorylated at the 5' end, or the amplified DNA product is phosphorylated at the 5' end after step 1) but before step 4).

2. A method of claim 1, wherein the dumbbell-shaped DNA is used as a vector for RNA transcription.

3. A method of claim 1, wherein the target DNA sequence contains at least one promoter sequence and an siRNA transcription sequence.

4. A method of claim 3, wherein the dumbbell-shaped DNA is a tandem-shaped siRNA expression vector or a stem loop-shaped siRNA expression vector.

5. A method of claim 1, wherein the sense primer and/or the antisense primer contains a first spacer sequence and a second spacer sequence, the first spacer and second spacer sequences being complementary to each other, and the first and second spacer sequences being connected so that they are in opposite directions to each other with the sequence (b) interposed.

6. A method of claim 1, wherein for the sense and antisense primers, the sequence (a) is TN1AGG (wherein T, A, and G represent thymine, adenine, and guanine, respectively, and N1 represents any one of adenine, cytosine, guanine, or thymine), the sequence (b) is (T)n (wherein T represents thymine and n is an integer of at least one), and the sequence (c) is CCTN11AGC (wherein C, T, A, and G represent cytosine, thymine, adenine, and guanine, respectively, and N11 represents any one of adenine, cytosine, guanine, or thymine).

7. A method of claim 6, wherein the sense and antisense primers further contain a first and a second spacer sequence, the first spacer sequence being represented by AG and the second spacer sequence by TC in the sense primer, and the first spacer sequence being represented by TC and the second spacer sequence by AG in the antisense primer, and in the sense and antisense primers, the first and second spacer sequences being connected so that they are in opposite directions to each other with sequence of (b) interposed.

8. A method of claim 7, wherein the sequence (b) is represented by TTTT in the sequences of the sense and antisense primers.

9. A method of claim 1, wherein the sense primer and/or the antisense primer is modified by a functional group in at least one position of the nucleic acid backbone or bases of sequence (b) and/or the spacer sequence.

10. A method of claim 9, further comprising a step of substituting a functional group after step 1).

* * * * *

SEQUENCE LISTING

```
<160> NUMBER OF SEQ ID NOS: 25

<210> SEQ ID NO 1
<211> LENGTH: 245
<212> TYPE: DNA
<213> ORGANISM: Artificial
<220> FEATURE:
<223> OTHER INFORMATION: synthetic DNA

<400> SEQUENCE: 1
aaggtcgggc aggaagaggg cctatttttcc atgattcctt catatttgca tatacgatac      60
aaggctgtta gagagataat tagaattaat ttgactgtaa acacaaagat attagtacaa     120
aatacgtgac gtagaaagta ataatttctt gggtagtttg cagttttaaa attatgtttt     180
aaaatggact atcatatgct taccgtaact tgaaagtatt tcgatttctt ggctttatat     240
atctt                                                                 245

<210> SEQ ID NO 2
<211> LENGTH: 104
<212> TYPE: DNA
<213> ORGANISM: Artificial
<220> FEATURE:
<223> OTHER INFORMATION: synthetic DNA

<400> SEQUENCE: 2
aatatttgca tgtcgctatg tgttctggga aatcaccata aacgtgaaat gtctttggat      60
ttgggaatct tataagttct gtatgagacc acagatcgat cccc                      104
```

<210> SEQ ID NO 3
<211> LENGTH: 86
<212> TYPE: DNA
<213> ORGANISM: Artificial
<220> FEATURE:
<223> OTHER INFORMATION: synthetic DNA

<400> SEQUENCE: 3
accgttggtt tccgtagtgt agtggttatc acgttcgcct aacacgcgaa aggtccccgg    60
ttcgaaaccg ggcactacaa aaacca                                         86

<210> SEQ ID NO 4
<211> LENGTH: 14
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 4
ggntggnngg ntgg                                                      14

<210> SEQ ID NO 5
<211> LENGTH: 15
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 5
ggntggnnng gntgg                                                     15

<210> SEQ ID NO 6
<211> LENGTH: 16
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

```
<400> SEQUENCE: 6
ggntggnnnn ggntgg                                               16

<210> SEQ ID NO 7
<211> LENGTH: 17
<212> TYPE: DNA
<213> ORGANISM: Artificial
<220> FEATURE:
<223> OTHER INFORMATION: synthetic DNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (7)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 7
ggntggnnnn nggntgg                                              17

<210> SEQ ID NO 8
<211> LENGTH: 15
<212> TYPE: DNA
<213> ORGANISM: Artificial
<220> FEATURE:
<223> OTHER INFORMATION: synthetic DNA

<400> SEQUENCE: 8
ggcgttcggg gggta                                                15

<210> SEQ ID NO 9
<211> LENGTH: 63
<212> TYPE: DNA
<213> ORGANISM: Artificial
<220> FEATURE:
<223> OTHER INFORMATION: synthetic DNA

<400> SEQUENCE: 9
ggctatgtct aggagtgtac ctagaattac atcaagggag atggtgcgct cctggacgta    60
gcc                                                                 63

<210> SEQ ID NO 10
<211> LENGTH: 53
<212> TYPE: DNA
<213> ORGANISM: Artificial
<220> FEATURE:
<223> OTHER INFORMATION: synthetic DNA

<400> SEQUENCE: 10
gggtaattgg tagattaagc ggtgtgctgt cccgcttgat ctgccaattg ccc           53

<210> SEQ ID NO 11
<211> LENGTH: 43
<212> TYPE: DNA
<213> ORGANISM: Artificial
<220> FEATURE:
<223> OTHER INFORMATION: synthetic DNA

<400> SEQUENCE: 11
gggaattcac ctgccggcga gggttttccc agtcacgacg ttg                     43
```

<210> SEQ ID NO 12
<211> LENGTH: 46
<212> TYPE: DNA
<213> ORGANISM: Artificial
<220> FEATURE:
<223> OTHER INFORMATION: synthetic DNA

<400> SEQUENCE: 12
ggctgcagac ctgccggcca ccgagcggat aacaatttca cacagg          46

<210> SEQ ID NO 13
<211> LENGTH: 34
<212> TYPE: DNA
<213> ORGANISM: Artificial
<220> FEATURE:
<223> OTHER INFORMATION: synthetic DNA

<400> SEQUENCE: 13
ggtgtgtccg cgttggcttt tgccaacgcg gaca          34

<210> SEQ ID NO 14
<211> LENGTH: 59
<212> TYPE: DNA
<213> ORGANISM: Artificial
<220> FEATURE:
<223> OTHER INFORMATION: synthetic DNA

<400> SEQUENCE: 14
cctcggccta tagtgagtcg tattaggcgg gaaccgccta atacgactca ctataggcc          59

<210> SEQ ID NO 15
<211> LENGTH: 41
<212> TYPE: DNA
<213> ORGANISM: Artificial
<220> FEATURE:
<223> OTHER INFORMATION: synthetic DNA

<400> SEQUENCE: 15
ttaggagttt tctcctaagc gttttcccag tcacgacgtt g          41

<210> SEQ ID NO 16
<211> LENGTH: 41
<212> TYPE: DNA
<213> ORGANISM: Artificial
<220> FEATURE:
<223> OTHER INFORMATION: synthetic DNA

<400> SEQUENCE: 16
ttaggagttt tctcctaagc gttttcccag tcacgacgtt g          41

<210> SEQ ID NO 17
<211> LENGTH: 41
<212> TYPE: DNA
<213> ORGANISM: Artificial
<220> FEATURE:
<223> OTHER INFORMATION: synthetic DNA

<400> SEQUENCE: 17
ttaggagttt tctcctaagc gttttcccag tcacgacgtt g          41

<210> SEQ ID NO 18
<211> LENGTH: 44
<212> TYPE: DNA
<213> ORGANISM: Artificial
<220> FEATURE:
<223> OTHER INFORMATION: synthetic DNA

<400> SEQUENCE: 18

```
ttaggtctttt tgacctaagc gagcggataa caatttcaca cagg           44

<210> SEQ ID NO 19
<211> LENGTH: 39
<212> TYPE: DNA
<213> ORGANISM: Artificial
<220> FEATURE:
<223> OTHER INFORMATION: synthetic DNA

<400> SEQUENCE: 19
gttttcccag tcacgacgtt gaaggtcggg caggaagag                  39

<210> SEQ ID NO 20
<211> LENGTH: 44
<212> TYPE: DNA
<213> ORGANISM: Artificial
<220> FEATURE:
<223> OTHER INFORMATION: synthetic DNA

<400> SEQUENCE: 20
gagcggataa caatttcaca caggaaaaag gctacgtcca ggag            44

<210> SEQ ID NO 21
<211> LENGTH: 417
<212> TYPE: DNA
<213> ORGANISM: Artificial
<220> FEATURE:
<223> OTHER INFORMATION: synthetic DNA

<400> SEQUENCE: 21
ttaggagttt tctcctaagc gttttcccag tcacgacgtt gaaggtcggg caggaagagg    60
gcctattttc catgattcct tcatatttgc atatacgata caaggctgtt agagagataa   120
ttagaattaa tttgactgta aacacaaaga tattagtaca aaatacgtga cgtagaaagt   180
aataatttct tgggtagttt gcagttttaa aattatgttt taaatgggac tatcatatgc   240
ttaccgtaac ttgaaagtat ttcgatttct tggctttata tatcttgtgg aaaggacgaa   300
acaccggcta tgtctaggag tgtacctaga attcatcaa gggagatggt gcgctcctgg    360
acgtagcctt tttcctgtgt gaaattgtta tccgctcgct taggtcaaaa gacctaa      417

<210> SEQ ID NO 22
<211> LENGTH: 93
<212> TYPE: DNA
<213> ORGANISM: Artificial
<220> FEATURE:
<223> OTHER INFORMATION: synthetic DNA

<400> SEQUENCE: 22
tttcccatga ttccttcata tttgcatctt accgtaactt gaaagtattt cgatttcttg    60
gctttatata tcttgtggaa aggacgaaac acc                                93

<210> SEQ ID NO 23
<211> LENGTH: 109
<212> TYPE: DNA
<213> ORGANISM: Artificial
<220> FEATURE:
<223> OTHER INFORMATION: synthetic DNA

<400> SEQUENCE: 23
tttcccatga ttccttcata tttgcatata ggactatcat atgcttaccg taacttgaaa    60
gtatttcgat tcttggctt tatatatctt gtggaaagga cgaaacacc                109
```

```
<210> SEQ ID NO 24
<211> LENGTH: 58
<212> TYPE: DNA
<213> ORGANISM: Artificial
<220> FEATURE:
<223> OTHER INFORMATION: synthetic DNA

<400> SEQUENCE: 24
gcagaagcta tgaaacgatt tgcttcctgt cacaaatcgt tcatagcttc tgcttttt       58

<210> SEQ ID NO 25
<211> LENGTH: 240
<212> TYPE: DNA
<213> ORGANISM: Artificial
<220> FEATURE:
<223> OTHER INFORMATION: synthetic DNA

<400> SEQUENCE: 25
tttcccatga ttccttcata tttgcatata cgatacaagg ctgttagaga gataattaga     60
attaatttgc ctgtaaacac aaagatatta gtacaaaata cgtgacgtag aaagtaataa    120
tttcttgggt agtttgcagt tttaaaatta tgttttaaaa tggactatca tatgcttacc    180
gtaacttgaa agtatttcga tttcttggct ttatatatct tgtggaaagg acgaaacacc    240
```